(12) United States Patent
Widegren et al.

(10) Patent No.: US 12,281,058 B2
(45) Date of Patent: *Apr. 22, 2025

(54) MANGANESE CATALYSTS AND THEIR USE IN HYDROGENATION OF KETONES

(71) Applicant: University Court of the University of St Andrews, Fife (GB)

(72) Inventors: Magnus Widegren, Fife (GB); Matthew Lee Clarke, Fife (GB)

(73) Assignee: UNIVERSITY COURT OF THE UNIVERSITY OF ST ANDREWS, Fife (GB)

( * ) Notice: Subject to any disclaimer, the term of this patent is extended or adjusted under 35 U.S.C. 154(b) by 925 days.

This patent is subject to a terminal disclaimer.

(21) Appl. No.: 17/421,251

(22) PCT Filed: Jan. 8, 2020

(86) PCT No.: PCT/GB2020/050035
§ 371 (c)(1),
(2) Date: Jul. 7, 2021

(87) PCT Pub. No.: WO2020/144476
PCT Pub. Date: Jul. 16, 2020

(65) Prior Publication Data
US 2022/0119329 A1    Apr. 21, 2022

(30) Foreign Application Priority Data
Jan. 8, 2019  (GB) ..................................... 1900253

(51) Int. Cl.
C07C 29/156    (2006.01)
B01J 31/18     (2006.01)
C07F 17/02     (2006.01)

(52) U.S. Cl.
CPC ......... C07C 29/156 (2013.01); B01J 31/1815 (2013.01); B01J 31/189 (2013.01); C07F 17/02 (2013.01); B01J 2231/643 (2013.01); B01J 2531/0205 (2013.01); B01J 2531/72 (2013.01); B01J 2531/842 (2013.01)

(58) Field of Classification Search
CPC ... C07C 29/156; B01J 31/1815; B01J 31/189; B01J 2231/643; B01J 2531/0205; B01J 2531/72; B01J 2531/842; C07F 17/02
See application file for complete search history.

(56) References Cited

U.S. PATENT DOCUMENTS

2021/0053932 A1    2/2021   Widegren et al.

FOREIGN PATENT DOCUMENTS

CN    103012498 A       4/2013
WO    WO 2006/068879 A1 6/2006

OTHER PUBLICATIONS

Clayden, "Organic Chemistry—Determining Reaction Mechanisms", Organic Chemistry—Determining Reaction Mechanisms, Oxford University, Jan. 2001, pp. 1091-1092.
Examination Report for corresponding European Application No. 20701092.7, dated Oct. 18, 2022, 5 pages.
Rice, "Inductive Effects of Alkyl Groups", LibreTexts, Jan. 2002, https://batch.libretexts.org/print/url=https://chem.libretexts.org/Bookshelves/Organic_Chemistry/Supplemental_Modules_(Organic Chemistry)/Arenes/Properties_of_Arenes/Inductive_Effects_of_Alkyl_Groups.pdf, retrieved on Sep. 23, 2022, 5 pages.
PCT International Preliminary Report on Patentability for corresponding PCT Application No. PCT/GB2020/050035, mailed on Jul. 22, 2021, 8 pages.

(Continued)

Primary Examiner — Daniel R Carcanague
(74) Attorney, Agent, or Firm — Dority & Manning, P.A.

(57) ABSTRACT

The invention provides a method comprising hydrogenating a ketone in the presence of (i) a base, (ii) hydrogen gas and (iii) a catalyst comprising a charged or neutral complex of formula (I):

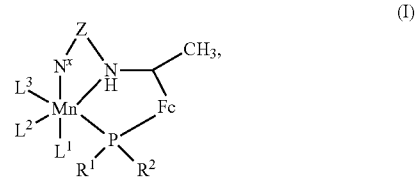

wherein:
Mn is a manganese atom or a manganese ion in oxidation state (I) to (VII);

$R^1$ and $R^2$ are each independently optionally substituted $C_{4-8}$monocyclic aryl or $C_{3-7}$monocyclic heteroaryl moieties;

-Fc- denotes a ferrocene (bis($\eta^5$-cyclopentadienyl)iron) moiety covalently bonded via adjacent carbon atoms of one of the two cyclopentadienyl moieties, and which may be optionally further substituted, in either cyclopentadienyl ring;

—Z— is an alkylene linker of the formula —$(CH_2)_{1-6}$— in which one or more of the hydrogen atoms of the alkylene may be independently substituted;

—$N^x$ is an optionally substituted nitrogen-containing heteroaryl moiety, with the proviso that at least one of $R^1$, $R^2$ and —$N^x$ is substituted one or more times with an electron donating group; and $L^1$-$L^3$ constitute one, two or three ligands, wherein, when the complex of formula (I) is charged, the catalyst comprises one or more additional counterions to balance the charge of the complex.

20 Claims, No Drawings

(56) References Cited

OTHER PUBLICATIONS

PCT International Search Report and Written Opinion for corresponding PCT Application No. PCT/GB2020/050035, mailed on Mar. 16, 2020, 10 pages.
Blaser et al., "Solvias Josiphos ligands: from discovery to technical applications", Topics in Catalysis vol. 19, No. 1, Mar. 2002, 14 pages.
Diaz-Valenzuela et al., "Enantioselective Hydrogenation and Transfer Hydrogenation of Bulky Ketones Catalysed by a Ruthenium Complex of a Chiral Tridentate Ligand", Chemistry European Journal 2009, 15, Dec. 15, 2008, pp. 1227-1232.
Docherty et al., "Activation and discovery of earth-abundant metal catalysts using sodium tert-butoxide", Nature Chemistry Articles vol. 9, Jan. 9, 2017, 7 pages.
Garbe et al., "Manganese(I)-Catalyzed Enantioselective Hydrogenation of Ketones Using a Defined Chiral PNP Pincer Ligand", Angew. Chem. Int. Ed., vol. 56, 2017, pp. 11327-11241.
Hou et al., "Sterically Hindered Chiral Ferrocenyl P, N,N-Ligands for Highly Diastereo-/Enantioselective Ir-Catalyzed Hydrogenation of a-Alkyl-B-ketoesters via Dynamic Kinetic Resolution", Organic Letters, ACS Publications, vol. 18, Oct. 21, 2016, pp. 5592-5595.
Moss et al., "Glossary of Class Names of Organic Compounds and Reactive Intermediates Based on Structure", Pure & Applied Chemistry, vol. 67, Nos. 8/9, 1995, pp. 1307-1375.
Nguyen et al., "Manganese Pincer Complexes for the Base-Free, Acceptorless Dehydrogenative Coupling of Alcohols to Esters: Development, Scope, and Understanding", ACS Catalysis, vol. 7, Jan. 30, 2017, pp. 2022-2032.
Noyori et al., "Asymmetric Catalysis by Architectural and Functional Molecular Engineering: Practical Chemo- and Stereoselective Hydrogenation of Ketones", Angewandte Chem. Int. Ed. vol. 40, 2001, pp. 40-73.
Vasilenko et al., "Mechanism-Based Enantiodivergence in Manganese Reduction Catalysis: A Chiral Pincer Complex for the Highly Enantioselective Hydroboration of Ketones", Angew. Chem, Int. Ed. Vol. 56, 2017, pp. 8393-8397.
Werkmeister et al., "Catalytic Hydrogenation of Carboxylic Acid Esters, Amides, and Nitriles with Homogenous Catalysts", Organic Process Research & Development, ACS Publications, vol. 18, Jan. 13, 2014, pp. 289-302.
Widegren et al., "A highly active manganese catalyst for the hydrogenation of ketones and esters: enantioselective reduction catalysis with manganese", Angewandte Chemie International Edition, vol. 56, Issue 21, Apr. 20, 2017, pp. 5825-5828.
Widegren et al., "Towards Practical Earth Abundant Reduction Catalysis: design of improved catalysts for manganese catalysed hydrogenation", Catalysis Science & Technology Journal, Sep. 16, 2019, 11 pages.
Wu et al., "Iridium Catalysts with f-Amphox Ligands: Asymmetric Hydrogenation of Simple Ketones", ACS Organic Letters, vol. 18, Jun. 3, 2016, pp. 2938-2941.
Yu et al., "Iridium-Catalyzed Asymmetric Hydrogenation of Ketones with Accessible and Modular Ferrocene-Based Amino-phosphine Acid (f-Ampha) Ligands", Organic Letters, ASC Publications, vol. 19, Jan. 17, 2017, pp. 690-693.
Yu et al., "Readily Accessible and Highly Efficient Ferrocene-Based Amnio-Phosphine-Alcohol (f- Amphol) Ligands for Iridium-Catalyzed Asymmetric Hydrogenation of Simple Ketones", Chemistry European Journal, vol. 23, 2017 pp. 970-975.
Zirakzadeh et al., "Enantioselective Transfer Hydrogenation of Ketones Catalyzed by a Manganese Complex Containing an Unsymmetrical Chiral PNP' Tridentate Ligand", ChemCatChem, vol. 9, 2017, pp. 1744-1748.
UK IPO Search Report for corresponding GB Application No. GB1900253.4, mailed on Jun. 25, 2019, 4 pages.
Appleton et al.. Rhodium (I) Complexes of Ferrocenylphosphines as Efficient Asymmetric Catalysts. The Structure of Fe($n^5$-$C_5H_3(P(CMe_3)_2$1,3)($n^5$-$C_5H_3(CHMeNMe_2)P(CMe_3)_1$1,2)*, Journal of Organometallic Chemistry, vol. 279, 1985, pp. 5-21.
Ling et al.. "Highly Enantioselective Synthesis of Chiral Benzhydrols via Manganese Catalyzed Asymmetric Hydrogenation of Unsymmetrical Benzophenones Using an Imidazole-Based Chiral PNN Tridentate Ligand", Organic Letters, vol. 21, 2019, pp. 3937-3941.
Ma et al., "Manganese-Catalyzed Asymmetric Hydrosilylation of Aryl Ketones", ACS Omega, vol. 2, 2017, pp. 4688-4692.
Nie et al., "Very Simple and Highly Modular Synthesis of Ferrocene-Based Chiral Phosphines with a Wide Variety of Substituents at the Phosphorus Atom(s)", Organometallics, vol. 33, 2014, pp. 2109-2114.
Nie et al., "Asymmetric hydration of aromatic ketones using an iridium(I) catalyst containing ferrocene-based P-N-N tridentate ligands", Tetrahedron: *Asymmetry*, vol. 24, 2013, pp. 1567-1571.
Wang et al., "Practical (asymmetric) transfer hydrogenation of ketones catalyzed by manganese with (chiral) diamines ligands", Catalysis Communications; vol. 105, 2018, pp. 31-36.
Widegren et al., "Manganese Catalyzed Hydrogenation of Enantiomerically Pure Esters", Organic Letters, vol. 20, 2018, pp. 2654-2658.

MANGANESE CATALYSTS AND THEIR USE IN HYDROGENATION OF KETONES

RELATED APPLICATIONS

The present application is the national stage entry of International Patent Application No. PCT/GB2020/050035 having a filing date of Jan. 8, 2020, which claims priority to United Kingdom Application Serial No. GB 1900253.4, filed on Jan. 8, 2019, the entire contents of which are incorporated by reference.

TECHNICAL FIELD OF THE INVENTION

The present invention relates to the field of manganese compounds and catalysts and their uses in catalytic hydrogenation, particularly in methods of manganese-catalysed hydrogenation of ketones to alcohols. Advantageously, where the ketone is prochiral, its asymmetric reduction may be achieved.

BACKGROUND OF THE INVENTION

The reduction of ketones to alcohols, is a fundamental transformation in organic chemistry, and is an integral part in the synthesis of a number of industrial products, including pharmaceuticals and fine chemicals.

Typical heterogeneous hydrogenation pre-catalysts include Raney nickel, and copper chromite, which require harsh reaction conditions. In contrast, the use of homogeneous catalysis, reviewed by S Werkmeister et al. (*Org. Process Res. Dev.*, 18, 289-302 (2014)) is generally considered to permit use of lower reaction temperatures and hydrogen pressures, giving rise to greater selectivity.

Effecting hydrogenation of ketones catalytically using molecular hydrogen is typically achieved using noble transition metal catalysts (for example, palladium- or ruthenium-based catalysts). The development of ruthenium catalysts for the reduction of ketones to alcohols, particularly with stereochemical control (for which the Nobel Prize in chemistry was awarded in 2001) is mature technology that is applicable at a commercial scale. These catalysts comprise of ruthenium with two bidentate ligands: a diphosphine and a diamine (see Noyori, R.; Ohkuma, T. *Angew. Chem. Int. Ed.* 2001, 40, 40). Ketones reduction catalysts based on tridentate ligands, comprising three donors contacting the ruthenium or iridium metal centre, often phosphorous and two nitrogens (see: Diaz-Valenzuela, M. B.; Phillips, S. D.; France, M. B.; Gunn, M. E.; Clarke, M. L. *Chem. Eur. J.* 2009, 15, 1227), or phosphorous, nitrogen and oxygen.

J. Yu et al. (see *Chem. Eur. J.*, 23, 970-975 (2017) and *Org. Lett.*, 19, 690-693 (2017)) describe the use of a series of iridium-based catalysts comprising ferrocene-based amino-phosphine-alcohol (f-Amphol) or ferrocene-based amino-phosphine-alcohol (f-Ampha) ligands for the asymmetric hydrogenation of simple ketones to afford the corresponding chiral alcohols with high enantioselectivities and conversions.

Increased use of noble transition metals is leading to their lower abundance and increased cost. Alternative hydrogenation catalysts based on their more abundant and inexpensive first row congeners for example iron or manganese, are advantageous.

D. Wang et al. (in *Catalysts Communications*, 105, 31-36 (2018)) describe the reduction of ketones with 2-propanol as a reductant, achieved using an in-situ generated catalytic system based on manganese pentacarbonyl bromide as a metal precursor, and ethylenediamine as ligand.

A. Zirakzadeh et al. (in *ChemCatChem.*, 9, 1744-1748 (2017)) describe the use of manganese complexes of the types [Mn(PNP')(Br)(CO)$_2$] and [Mn(PNP')(H)(CO)$_2$](containing a tridentate ligand with a planar chiral ferrocene and a chiral aliphatic unit) for the enantioselective transfer hydrogenations of ketones using dihydrogen. Similarly, M. Garbe et al. (*Angew. Chem. Int. Ed.*, 56, 11237-11241 (2017)) describe the use of chiral manganese PNP pincer complexes in the asymmetric hydrogenation of several prochiral ketones with molecular hydrogen.

M B Widegren, G J Harkness, A M Z Slawin, D B Cordes and M L Clarke (*Angew. Chem. Int. Ed.*, 56, 5825-5828 (2017)) describe the use of a hydrogenation catalyst based on a manganese complex of a chiral P,N,N ligand in the hydrogenation of esters and enantioselective hydrogenation of pro-chiral ketones.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

SUMMARY OF THE INVENTION

We have found that the manganese-based catalysts described herein, in which the P,N,N ligands are substituted with at least one electron donor group, are surprisingly and significantly more effective catalysts for ketone hydrogenation than the analogous unsubstituted complexes. Specifically, the complexes described herein are more reactive and effect ketone hydrogenation at rates that are faster than their unsubstituted analogues. This results in lower catalyst loadings being required.

Furthermore, we have found that, in contrast with their unsubstituted analogues, the manganese-based compounds described herein dissolve readily in a variety of solvents including environmentally benign economic solvents favoured by industry (for example, ethanol). This allows a greater flexibility in the choice of solvent to use when working with the compounds of the invention.

Viewed from a first aspect, therefore, the invention provides a method comprising hydrogenating a ketone in the presence of (i) a base, (ii) hydrogen gas and (iii) a catalyst comprising a charged or neutral complex of formula (I):

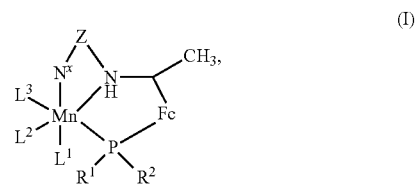

wherein:
Mn is a manganese atom or a manganese ion in oxidation state (I) to (VII);
R$^1$ and R$^2$ are each independently C$_{4-8}$monocyclic aryl or C$_{3-7}$monocyclic heteroaryl moieties, optionally substituted one or more times with a first electron donating group;

-Fc- denotes a ferrocene (bis($\eta^5$-cyclopentadienyl)iron) moiety covalently bonded via adjacent carbon atoms of one of the two cyclopentadienyl moieties, and which may be optionally further substituted, in either cyclopentadienyl ring, one or more times with a substituent selected from the group consisting of halo, aliphatic $C_{1-6}$hydrocarbyl, trihalomethyl, aryl, heteroaryl, hydroxy, nitro, amino, alkoxy, alkylthio, carboxylate, sulfonate, phosphate, cyano, thio, formyl, ester, acyl, thioacyl, carbamido and sulfonamido;

—Z— is an alkylene linker of the formula —$(CH_2)_{1-6}$— in which one or more of the hydrogen atoms of the alkylene may be independently substituted with an alkyl, aryl, heteroaryl, hydroxy, nitro, amino, alkoxy, alkylthio or thiol substituent;

—$N^x$ is a nitrogen-containing heteroaryl moiety, optionally substituted one or more times with a second electron donating group, with the proviso that at least one of $R^1$, $R^2$ and —$N^x$ is substituted one or more times with the first and/or second electron donating group respectively; and $L^1$-$L^3$ constitute one, two or three ligands in which each of $L^1$-$L^3$ independently represents a monodentate neutral or anionic ligand; or one of $L^1$-$L^3$ represents a monodentate neutral or anionic ligand and the other two of $L^1$-$L^3$ together represent a bidentate neutral or anionic ligand; or $L^1$-$L^3$ together represent a tridentate neutral or anionic ligand, wherein, when the complex of formula (I) is charged, the catalyst comprises one or more additional counterions to balance the charge of the complex.

Viewed from a second aspect, the invention provides a catalyst comprising a charged or neutral complex of formula (I) as defined in the first aspect, wherein —$N^x$ is substituted one or more times with the second electron donating group and at least one of $R^1$ and $R^2$ are substituted one or more times with the first electron donating group.

Viewed from a third aspect, the invention provides a compound comprising a charged or neutral complex of formula (I) as defined in the first aspect, wherein —$N^x$ is substituted one or more times with the second electron donating group and at least one of $R^1$ and $R^2$ are substituted one or more times with the first electron donating group.

Further aspects and embodiments of the present invention will become apparent from the detailed discussion of the invention that follows below.

DETAILED DESCRIPTION OF THE INVENTION

Throughout this specification the word "comprise", or variants such as "comprises" or "comprising", will be understood to imply the inclusion of a stated element, integer or step, or group of elements, integers or steps, but not the exclusion of any other element, integer or step, or group of elements, integers or steps.

The term "about", particularly in reference to a given quantity, is intended to encompass deviations of ±5%. For example both 47.5 and 94.5 are intended to fall within a range stated to be from about 50 to about 90.

According to the method of the invention, particular catalysts are used to catalyse the hydrogenation of ketones in the presence of bases. The expression "used to catalyse" herein indicates that that the catalyst is used to promote the hydrogenation reaction, with use of molecular hydrogen ($H_2$), in a substoichiometric amount (relative to the ketone substrate being hydrogenated), i.e. that the catalyst is present in an amount of less than 1 molar equivalent (100 mol %) relative to the ketone.

The expression "used to catalyse" does not require that the catalyst with which the ketone is contacted is the actual catalytic species, but simply that the catalyst is used in order to promote the hydrogenation reaction. The catalyst, defined as such in connection with the practice of this invention, may therefore be a so-called pre-catalyst, which may be converted to the actual catalytic species during the course of the hydrogenation reaction.

Catalysts which may be used in connection with the method of the invention can, for example, be prepared by mixing a manganese salt and additional ligand(s) appropriate to form a catalyst comprising a complex of formula (I), in the same reaction vessel in which a hydrogenation of the present invention is conducted. This is an example of an in situ preparative method. Alternatively, the catalyst may be prepared ex situ, by first forming an isolable complex, which may optionally be isolated, and then used as the catalyst in the method of the invention. Such ex situ-prepared catalysts may therefore be regarded as well-defined, the term well-defined denoting herein (as the term is used customarily in the art) a compound that has been isolated such that it is susceptible to characterisation (i.e. definition) and analysis (e.g. to determine its structure and degree of purity). In contrast, a catalyst that is not well-defined is one that is prepared without isolation from the medium (e.g. reaction medium) in which it is prepared, for example catalysts prepared in situ.

Typical substoichiometric amounts of catalysts that may be used in accordance with this invention will be in the range of about 0.00005 to about 10 mol %, e.g. about 0.0001 to about 5 mol %, often about 0.0001 to about 2 mol %, typically about 0.0005 to about 1 mol % relative to the molar amount of the ketone substrate. It will be understood that greater amounts of the catalyst will generally accelerate (i.e. promote to a greater extent) the hydrogenation reaction and that hydrogenation reactions may therefore be subject to routine optimisation by adjustment of the amount of catalyst used (as well as other features of the hydrogenation reaction described herein, for example concentration of the ketone in the reaction medium) in accordance with the normal ability of the skilled person.

In connection with the present invention, unless a particular context explicitly suggests to the contrary, the following definitions apply, which are considered to confirm the general understanding of a person of skill in the art. Where the meaning of a particular functional group used herein is not expressly defined, it is intended that such a term is likewise to be understood as it would by person of normal skill in the art, typically as evidenced by the publication of the Organic Chemical Division of the International Union of Pure and Applied Chemistry entitled "Glossary of class names of organic compounds and reactive intermediates based on structure" (*Pure & Appl. Chem.*, 67(8/9), 1307-1375 (1995)).

The term monocyclic is used herein to define a system having a single ring of atoms, for example pyridyl, phenyl or cyclohexyl.

Aryl denotes a monovalent group formed formally by abstraction of one hydrogen atom from an aromatic moiety (used synonymously herein with the term arene, to denote a mono- or polycyclic aromatic hydrocarbon). Analogously, heteroaryl denotes a monovalent group formed formally by abstraction of one hydrogen atom from a heteroaryl moiety (used synonymously herein with the term heteroarene, to denote a mono- or polycyclic heteroaromatic hydrocarbon).

Aryl groups are typically monocyclic groups, unless the context specifically dictates to the contrary, for example phenyl, although bicyclic aryl groups, such as naphthyl, and tricyclic aryl groups, such as phenanthryl and anthracyl, are also embraced by the term aryl. References to aromatic groups herein are to be similarly interpreted, i.e. as denoting monocyclic aromatic groups absent an express indication to the contrary.

As known to those skilled in the art, heteroaromatic moieties are derived formally from aromatic moieties by substitution of one or more (generally one or two) heteroatoms, typically O, N or S, in place of one or more carbon atoms together with any hydrogen atoms attached thereto. Illustrative heteroaromatic moieties include pyridine, furan, pyrrole and pyrimidine. Further examples of heteroaromatic rings include pyridazine (in which two nitrogen atoms are adjacent in an aromatic 6-membered ring); pyrazine (in which two nitrogens are 1,4-disposed in a 6-membered aromatic ring); pyrimidine (in which two nitrogen atoms are 1,3-disposed in a 6-membered aromatic ring); or 1,3,5-triazine (in which three nitrogen atoms are 1,3,5-disposed in a 6-membered aromatic ring).

Heteroaryl groups are typically monocyclic groups, unless the context specifically dictates to the contrary, for example pyridyl, although bicyclic heteroaryl groups, for example such as indolyl, are also embraced by the term heteroaryl. References to heteroaromatic groups herein are to be similarly interpreted, i.e. as denoting monocyclic heteroaromatic groups absent an express indication to the contrary.

The term electron donating group is well known in the art and is used herein to refer to an atom or functional group that donates electron density into a system. In the complexes described herein, the system is a conjugated π system and electron donation is via resonance or inductive effects, thus making the π system more nucleophilic. Any group capable of electron donation into such a system lies within the definition of an electron donating group.

The first and second electron donating group may be any one or a combination of substituents selected from the group consisting of amino, $C_{1-6}$alkyl, $C_{1-6}$alkyloxy, hydroxy and amido.

By $C_{1-6}$hydrocarbyl is meant an aliphatic or aromatic radical comprising hydrogen atoms and from 1 to 6 carbon atoms. Where aliphatic, the hydrocarbyl may be straight-chain or branched and/or comprise one or more sites of unsaturation (e.g. one or more carbon-carbon double or triple bonds). For example, a $C_{1-6}$hydrocarbyl moiety may be a $C_{1-6}$alkyl, $C_{2-6}$alkenyl, $C_{2-6}$alkynyl or $C_{3-6}$cycloalkyl moiety. Alternatively or additionally, hydrocarbyl moieties may be cyclic or a portion of their structure may be cyclic. For example, cyclopentylmethyl and cyclopentenylmethyl are both examples of an aliphatic $C_6$hydrocarbyl.

Often, but not necessarily, hydrocarbyl moieties described herein are saturated and aliphatic, i.e. are straight-chain and/or branched, cyclic or comprise one or more cyclic portions within a straight-chain or branched architecture.

By "halide" reference is being made to fluoride, chloride, bromide or iodide, typically chloride, bromide or iodide. Likewise, halo denotes fluoro, chloro, bromo or iodo, typically chloro, bromo or iodo.

Often but not necessarily, trihalomethyl denotes trifluoromethyl.

By amino is meant herein a group of the formula —N($R^4$)$_2$, wherein each $R^4$ independently denotes hydrogen or $C_{1-6}$hydrocarbyl or heteroaryl, or the two $R^4$ moieties together form an alkylene diradical, derived formally from an alkane from which two hydrogen atoms have been abstracted, typically from terminal carbon atoms, whereby to form a ring together with the nitrogen atom of the amine (forming, for example, pyrrolidinyl). Where $R^4$ is other than hydrogen (including those embodiments where the two $R^4$ moieties together form an alkylene diradical), one or more of its carbon atoms may be optionally substituted one or more times. In those embodiments where the two $R^4$ moieties together form an alkylene diradical and one or more the carbon atoms of $R^4$ are optionally substituted one or more times, this may form, for example, morpholinyl. The carbon atoms of $R^4$ may be optionally substituted one or more times with one or more substituents independently selected from the group consisting of halo, $C_{1-6}$hydrocarbyl, trihalomethyl, aryl, heteroaryl, hydroxy, nitro, amino, alkoxy, alkylthio, carboxylate, sulfonate, phosphate, cyano, thio, formyl, ester, acyl, thioacyl, carbamido and sulfonamido, more typically the optional substituents are selected from the group consisting of halo, $C_{1-6}$hydrocarbyl, trihalomethyl, aryl and heteroaryl.

Typically, amino herein denotes —N($R^4$)$_2$, wherein each $R^4$ independently denotes $C_{1-6}$hydrocarbyl or hydrogen. Often, amino denotes simple dialkylamino or monoalkyl-moieties (for example the dialkylamino moiety dimethylamino (—N(CH$_3$)$_2$), or di-tert-butylamino ((—N(C(CH$_3$)$_3$)$_2$)).

References to amino herein are also to be understood as embracing within their ambit quaternised or protonated derivatives of the amines resultant from compounds comprising such amino groups. Examples of the latter may be understood to be salts such as hydrochloride salts.

Alkoxy (synonymous with alkyloxy) and alkylthio moieties are of the formulae —O$R^5$ and —S$R^5$ respectively, wherein $R^5$ is a saturated aliphatic hydrocarbyl group, typically a $C_{1-6}$alkyl or $C_{3-6}$cycloalkyl group, optionally substituted with one or more substituents selected from the group consisting of halo, aryl and heteroaryl.

By carboxylate, sulfonate and phosphate are meant herein the functional groups —CO$_2^-$, —SO$_3^-$ and —PO$_4^{2-}$ respectively, which may be in their protonated forms.

By formyl is meant a group of formula —C(H)O.

By ester is meant a functional group comprising the moiety —OC(=O)—.

By acyl is meant the functional group of formula —C(O)$R^5$, wherein $R^5$ is as hereinbefore defined. Analogously, thioacyl denotes a functional group of the formula —C(O)$R^5$, again wherein $R^5$ is as hereinbefore defined.

By carbamido is meant herein a functional group, either of formula —NHCOR$^5$ or of formula —CONHR$^5$, wherein $R^5$ is as hereinbefore defined. Analogously, sulfonamido denotes a functional group, either of formula —NHSO$_2$R$^5$, or of formula —SO$_2$NHR$^5$, wherein $R^5$ is as hereinbefore defined.

The term amido is used herein to define a functional group of formula —NHCOR5, wherein $R^5$ is as hereinbefore defined.

Where a ligand is stated to be monodentate, it is capable of coordinating (i.e. to the manganese centre) through one donor site. Where a ligand is bidentate, it is capable of coordinating through two discrete donor sites.

The catalyst used in accordance with the invention is characterised by comprising a complex of formula (I), as described herein. The nature of the complex is discussed in detail below.

Although (without wishing to be bound by theory) the catalytic species that constitutes the starting point of the catalytic hydrogenation reaction may be one comprising a manganese ion in oxidation state (I), it is well-known in the field of transition metal catalysis that initial pre-catalysts may be presented with a transition metal centre in a variety of oxidation states. These may be converted, with appropriate oxidation or reduction of the transition metal (here a manganese) atom or ion to a catalytically active species during the course of the reaction being catalysed, i.e. with any necessary oxidation or reduction of the manganese centre. Appropriate oxidation or reduction of the manganese atom or ion may be achieved, for example, with a suitable reducing or oxidising agent, or reactive ligand.

Two examples of the uses of manganese (II) pre-catalysts in which the manganese is present in oxidation state (II), different to that of the active catalytic species, are described by V Vasilenko et al. (*Angew. Chem. Int. Ed.*, 56, 8393-8397 (2017)) in connection with the hydroboration of ketones and X Ma et al. (*ACS Omega*, 2, 4688-4692 (2017)) in connection with the hydrosilylation of aryl ketones.

Moreover, it is well known that manganese (0) species such as $Mn_2(CO)_{10}$ undergo oxidation to the desired Mn species. Indeed, Nguyen et al. report on such an oxidation with amino ligand to produce reduction catalysts (*ACS Catal.*, 7, 2022-2032 (2017)).

While there is no necessity to employ a higher oxidation state Mn precursor, reduction of high oxidation state manganese (e.g. in the context of oxidation reagents) to Mn(II) is well-known. Even simple alkoxide salts can reduce higher valent metal salts to the desired low valent species, see JH Docherty et al. (*Nature Chemistry*, 9, 595-600 (2017)). Accordingly, with the appropriate reducing agents, manganese-containing compounds in oxidation states>(II) may be expected to be of use in conjunction with the present invention.

The complex of formula (I) may therefore comprise a manganese atom or a manganese ion in oxidation state (I) to (VII), typically a manganese ion, often a manganese ion in oxidation state (I) or (II), and very often a manganese ion in oxidation state (I).

Although in accordance with the present invention we find the use of the commercially available manganese (I) salt bromopentacarbonylmanganese (I) (Mn $Mn(CO)_5Br$) convenient, it will be understood that other commercially available (for example manganese (0) carbonyl ($Mn_2(CO)_{10}$)) or readily accessible manganese compounds may also be used to prepare complexes for use in the method of the invention.

As is evident from the structure of the complex of formula (I), $R^1$ and $R^2$ are substituents of the phosphine moiety within the tridentate ligand of formula $R^1(R^2)PFcC(CH_3)N(H)ZN^x$ within the complex of formula (I). As will be understood by those skilled in the art, there is generally the possibility to significantly vary within such ligands, inter alia, the substituents $R^1$ and $R^2$ of such phosphino moieties. Routine variation of these, for example through variation in steric bulk around and/or electronic influences upon the phosphorus atoms of such phosphino moieties, allows the skilled person to optimise such ligands in catalysts and complexes comprising these for any given reaction.

For example, the $R^1$ and $R^2$ ligands may be aliphatic or aromatic (or heteroaromatic) with significant substitution possible, without disrupting the function of catalysts comprising such moieties in their role as hydrogenation catalysts. Moreover, there exists a large variety of commercially available or otherwise easily accessible phosphorus-containing reagents from which $R^1$- and $R^2$-containing ligands may be prepared. Still further, it has been demonstrated in the art both that a variety of relevant ligands can be made and that complexes comprising these (including ferrocene-based PNN tridentate ligands of the formula $R^1(R^2)PFcC(CH_3)N(H)ZN^x$ defined in formula (I) herein) may be used in the context of catalytic hydrogenation reactions. For example, H Nie et al. (*Tetrahedron: Asymmetry.*, 24, 1567-1571 (2013) and Organometallics, 33, 2109-2114 (2014)) describe variation in the substitution of phenyl groups within the terminal diphenylphosphino moieties of such ligands, e.g. with a variety of alkyl substitution.

When constructing diphenylphosphino-substituted ferrocenes, Nie et al. describe introduction of the diphenylphosphino moiety via selective lithiation ortho to a substituent corresponding to the —$C(CH_3)N$— fragment within the tridentate ligand of formula $R^1(R^2)PFcC(CH_3)N(H)ZN^x$, within the complex of formula (I) defined herein, followed by treatment with a variety of chlorodiaryphosphines. In view of the huge variety of analogous electrophilic chlorophosphines that are available to the skilled person, it is well within his routine ability to prepare related ligands having other substituents on the phosphorus atom, for example optionally substituted aliphatic, heteroaryl and other aryl $R^1$ and $R^2$ moieties, for example to allow access to dialkylphosphino-containing ligands such as diethylphosphino- and ditert-butylphosphino-.

As detailed in the experimental section below, we have synthesised a ligand of formula $R^1(R^2)PFcC(CH_3)N(H)ZN^x$ in which $ZN^x$ is 2-pyridylmethyl by reaction between a N,N-dimethyl-1-ethylamino-substituted ferrocene in the presence of acetic anhydride and 2-picolylamine (2-aminomethylpyridine). We have also synthesised a ligand of formula $R^1(R^2)PFcC(CH_3)N(H)ZN^x$ in which $ZN^x$ is 4-dimethylaminopyridin-2-ylmethyl by reaction between a 1-ethylamino-substituted ferrocene with 4-dimethylamino-2-formylpyridine in the presence of sodium borohydride. Furthermore, as an example to illustrate the accessibility of complexes of formula (I), we note that the commercial availability of alternatively substituted ferrocenes, sold under the trade name PFA from Solvias AG, Switzerland, makes straightforward the synthesis of alternative $R^1$- and $R^2$-substituted ligands of formula $R^1(R^2)PFcC(CH_3)N(H)ZN^x$ by substitution of a different commercially available ferrocene to (S)-1-[Bis(4-methoxy-3,5-dimethylphenyl)phosphino]-2-[(R)-1-(DMA)ethyl]ferrocene or ((R)-1-[(S)-1-(dimethylamino)ethyl]-2-(diphenylphosphino) ferrocene) the use of which is described herein.

In particular, the following ferrocenes are commercially available from Solvias (in which DMA denotes dimethylamino):

(S)-1-[(R)-1-(DMA)ethyl]-2-(diphenylphosphino)ferrocene;
(R)-1-[(S)-1-(DMA)ethyl]-2-(diphenylphosphino)ferrocene;
(R)-1-[Bis(4-methoxy-3,5-dimethylphenyl)phosphino]-2-[(S)-1-(DMA)ethyl]ferrocene;
(S)-1-(Difuranylphosphino)-2-[(R)-1-(DMA)ethyl]ferrocene;
(R)-1-(Difuranylphosphino)-2-[(S)-1-(DMA)ethyl]ferrocene;
(S)-1-[Bis[3,5-bis(trifluoromethyl)phenyl]phosphino]-2-[(R)-1-(DMA)ethyl]ferrocene;
(R)-1-[Bis[3,5-bis(trifluoromethyl)phenyl]phosphino]-2-[(S)-1-(DMA)ethyl]ferrocene;
(S)-1-(Dicyclohexylphosphino)-2-[(R)-1-(DMA)ethyl]ferrocene; and (R)-1-(Dicyclohexylphosphino)-2-[(S)-1-(DMA)ethyl]ferrocene.

These may be used to provide a complex for use in accordance with the present invention in which the $R^1R^2P$-Fc-CH(Me)-NH— moiety of the complex of formula (I) is:
(S)-1-[(R)-1-(HN)ethyl]-2-(diphenylphosphino)ferrocene;
(R)-1-[(S)-1-(HN)ethyl]-2-(diphenylphosphino)ferrocene;
(S)-1-[Bis(4-methoxy-3,5-dimethylphenyl)phosphino]-2-[(R)-1-(HN)ethyl]ferrocene;
(R)-1-[Bis(4-methoxy-3,5-dimethylphenyl)phosphino]-2-[(S)-1-(HN)ethyl]ferrocene;
(S)-1-(Difuranylphosphino)-2-[(R)-1-(HN)ethyl]ferrocene;
(R)-1-(Difuranylphosphino)-2-[(S)-1-(HN)ethyl]ferrocene;
(S)-1-[Bis[3,5-bis(trifluoromethyl)phenyl]phosphino]-2-[(R)-1-(HN)ethyl]ferrocene;
(R)-1-[Bis[3,5-bis(trifluoromethyl)phenyl]phosphino]-2-[(S)-1-(HN)ethyl]ferrocene;
(S)-1-(Dicyclohexylphosphino)-2-[(R)-1-(HN)ethyl]ferrocene; or
(R)-1-(Dicyclohexylphosphino)-2-[(S)-1-(HN)ethyl]ferrocene, i.e. in which the dimethylamino (DMA) moiety is replaced with the NH moiety within the tridentate ligands of formula $R^1(R^2)PFc$-CH(Me)-N(H)ZN$^x$ described herein.

The present invention is exemplified herein with the use of a chiral catalyst because of the commercial availability of this catalyst in non-racemic form. The hydrogenation described herein may or may not generate a new stereogenic centre depending on whether or not the ketone substrate employed is pro-chiral. If the ketone employed is pro-chiral and control of the enantiomeric excess of the optically-active alcohol product is desirable, then it is advantageous to use a non-racemic form of the ligand to prepare a non-racemic complex of formula (I). Alternatively, if the enantiomeric excess of the optically-active alcohol product is of no concern or if the ketone employed is not pro-chiral then there is no advantage or disadvantage to using mixtures of enantiomers of chiral ligands in the preparation of complexes of formula (I).

The term pro-chiral defines an achiral compound that is capable of becoming chiral in a single desymmetrization step. As used herein, pro-chiral ketones are ketones that undergo hydrogenation to form optically-active alcohols. In other words, pro-chiral ketones are any ketones of formula $R^6(CO)R^7$, wherein $R^6$ and $R^7$ are chemically inequivalent.

Although a wide range of $R^1$ and $R^2$ are both accessible synthetically, and useful in accordance with the hydrogenation of the present invention, according to particular embodiments of the present invention $R^1$ and $R^2$ are each independently optionally substituted $C_{4-6}$monocyclic aryl or $C_{3-5}$monocyclic heteroaryl moieties, for example optionally substituted phenyl or furanyl moieties. Both phenyl, or furanyl, and in particular phenyl moieties, as well as other $C_{4-6}$monocyclic aryl or $C_{3-5}$monocyclic heteroaryl possibilities for $R^1$ and $R^2$, may be independently unsubstituted or substituted one or more times with a first electron donating group.

According to particular embodiments, the first electron donating group is any one or a combination of substituents selected from the group consisting of amino, $C_{1-6}$alkyl, $C_{1-6}$alkyloxy and hydroxy. Typically, the first electron donating group is any one or a combination selected from the group consisting of $C_{1-6}$alkyl and $C_{1-6}$alkyloxy substituents.

The $C_{1-6}$alkyl is often selected from any one of the group consisting of methyl, ethyl, isopropyl and tert-butyl and the $C_{1-6}$alkoxy is often selected from any one of the group consisting of methoxy, ethoxy, isopropoxy and tert-butoxy.

Preferably, the first electron donating group is a combination, i.e. $R^1$ and $R^2$ are optionally substituted two or more times with a combination of first electron donating groups. Typically, $R^1$ and $R^2$ are optionally substituted two or more times with methyl and methoxy groups. Often, when $R^1$ and $R^2$ are optionally substituted phenyl moieties, they are independently optionally substituted with $C_{1-6}$alkoxy groups at the para (C4 position) position and with $C_{1-6}$alkyl groups at the meta positions (C3 position(s)).

According to specific embodiments, moieties which can independently constitute $R^1$ and $R^2$ are 4-methoxy-3,5-dimethylphenyl, 4-methoxy-3,5-di-tert-butylphenyl or phenyl. According to these and other $R^1$ and $R^2$ moieties, both $R^1$ and $R^2$ will generally, but not necessarily, be the same moiety.

Analogously to the flexibility of access, synthetically, to a variety of $R^1$ and $R^2$ moieties, the skilled person has access to complexes of formula (I) comprising a large variety of Fc moieties, with relevant reagents both available commercially (see supra with respect to the reagents commercially available from Solvias), but also which may be incorporated within complexes of formula (I) using methodology of which the skilled person is well aware. In this regard, TD Appleton et al. (*J. Organomet. Chem.*, 279(1-2), 5-21 (1985)) describe ready functionalisation of the cyclopentadiene rings of ferrocene.

According to particular embodiments of the invention, one or more carbon atoms of either cyclopentadienyl ring of the ferrocene moiety Fc may be substituted with one or more halo and/or $C_{1-6}$alkyl substituents, in addition that is to the inherent substitution of the Fc moiety at those carbon atoms of one of its cyclopentadienyl rings, which connect Fc with the remainder of the complex of formula (I). According to still more particular embodiments of the invention, however, neither cyclopentadienyl ring of the Fc moiety within formula (I) is substituted (other than the inherent substitution through the ferrocene's points of connectivity with the remainder of the complex of formula (I) that is).

Access to the CH(Me) moiety within the complex of formula (I) that is adjacent to the Fc moiety is readily available to the skilled person owing to the commercial availability of what is known in the art as Ugi's amine (N,N-dimethyl-1-ferrocenylethylamine), available as either enantiomer.

N,N-dimethyl-1-ferrocenylethylamine may be reacted, using methodology described for example by H Nie et al. (supra), to access the corresponding 2-phosphino derivatives (which may incorporate the $R^1$ and $R^2$ moieties described herein), by selection of an appropriate chlorophosphine as described above. The N,N-dimethylamino moieties of the resultant 2-phosphino derivatives may then be transformed to the corresponding unsubstituted amino moieties before effecting reductive amination with an appropriate $N^x$-containing aldehyde (wherein $N^x$ is as defined herein), as also described by H Nie et al. (supra) and described herein to allow access to ligands of formula $R^1(R^2)PFc$-CH(Me)-NH—Z—$N^x$ described herein.

Alternatively, as described herein, the unsubstituted amino moieties may be reacted with an amine of formula $N^x$—Z—$NH_2$, wherein $N^x$ and Z are as defined herein, in order to access the ligands of formula $R^1(R^2)PFc$-CH(Me)-NH—Z—$N^x$. It will be understood that variation of either the aldehyde or amine of formula $N^x$—Z—$NH_2$ will allow access to variations of the —Z—$N^x$ terminus of the ligands of formula $R^1(R^2)PFc$-CH(Me)-NH—Z—$N^x$. More generally, a wide variety of compounds of formula $R^1(R^2)PFc$-CH(Me)-LG, wherein LG is a leaving group such as acetate or $NMe_2$, are accessible to the skilled person. These may then be converted to the ligands of formula $R^1(R^2)PFc$-CH(Me)-NH—Z—$N^x$ through the methodologies described herein. Accordingly, it is readily within the normal ability of the skilled person to access ligands of formula $R^1(R^2)PFc$-CH(Me)-NH—Z—$N^x$.

Still further, additional ways and strategies for incorporating into the ferrocene a structurally diverse array of substituents may be appreciated with reference to HU Blaser et al. (*Topics in Catalysis*, 19(1), 3-16 (2002)), which provides further teaching of assistance to the skilled person, in particular with respect to variation of the CH(Me)-NH—Z—$N^x$ portion of the ligands of formula $R^1(R^2)PFc$-CH(Me)-NH—Z—$N^x$.

In the complexes of formula (I), —Z— is an alkylene linker of the formula —$(CH_2)_{1-6}$-in which one or more of the hydrogen atoms of the alkylene may be independently substituted with an alkyl, aryl, heteroaryl, hydroxy, nitro, amino, alkoxy, alkylthio or thiol substituent. Access to variations in such linkers may be achieved, for example by reacting compounds of formula $R^1(R^2)PFc$-CH(Me)-LG, as described above, for example in which LG=$NMe_2$, with different primary amines having Z groups other than methylene (—$CH_2$—) as is present in 2-picolylamine. (Analogously, it will be appreciated that access to different $N^x$ groups may additionally (to varying the Z group that is) or alternatively be achieved by reacting compounds of formula $R^1(R^2)PFc$-CH(Me)-LG with different primary amines having $N^x$ groups other than the 2-pyridyl present in 2-picolylamine).

An alternative strategy to vary the —Z— groups in the complexes of formula (I) may be appreciated by consultation of C-J Hou and X—P Hu (*Org. Lett.*, 18, 5592-5595 (2016)) in which the authors describe ligands of formula $R^1(R^2)PFc$-CH(Me)-NH—Z—$N^x$ wherein the —Z— moiety may be a substituted methylene linker (for example by reaction of 1-(2-pyridinyl)ethylmethanesulfonate with a compound of formula $R^1(R^2)PFc$-CH(Me)-$NH_2$ (whereby to provide a methyl-substituted methylene linker —Z—)); or by condensing various 2-acylpyridines with the same compound of formula $R^1(R^2)PFc$-CH(Me)-$NH_2$ followed by hydrogenation of the resultant Schiff bases (whereby to provide a series of substituted methylene linkers —Z— in which the substituent corresponds to the R group in the 2-acylpyridines of formula 2-PyC(=O)R). (Analogously, it will be appreciated that access to $N^x$ groups different to 2-pyridyl may additionally (to varying the Z group that is) or alternatively be achieved by reacting compounds of formula $R^1(R^2)PFc$-CH(Me)-$NH_2$ with derivatives of the 1-(2-pyridinyl)ethylmethanesulfonate and the 2-acylpyridines having $N^x$ groups other than 2-pyridyl).

According to particular embodiments of the invention, —Z— is of the formula —$(CH_2)$—, —$(CHR^3)$— or —$(CH_2)_2$—, wherein $R^3$ is an alkyl, aryl, heteroaryl, hydroxy, nitro, amino, alkoxy, alkylthio or thiol substituent. According to particular embodiments of the invention, —Z— is of the formula —$(CH_2)$—, —$(CHR^3)$— or —$(CH_2)_2$—, wherein $R^3$ is a $C_{1-6}$alkyl substituent or phenyl optionally substituted one or more times with $C_{1-6}$alkyl and/or halo. According to other embodiments, —Z— is of the formula —$(CH_2)$—, —$(CHR^3)$— or —$(CH_2)_2$—, wherein $R^3$ is methyl or phenyl optionally substituted one or more times with $C_{1-6}$alkyl and/or halo.

Often (but not necessarily in view of the discussion herein of the availability of substituted alkylene linkers of formula —Z—), —Z— is unsubstituted. For example, —Z— may be of the formula —$(CH_2)$— or —$(CH_2)_2$—, often —$(CH_2)$—.

Various ways in which the $N^x$ moiety within the ligands of formula $R^1(R^2)PFc$-CH(Me)-NH—Z—$N^x$ may be varied have been described above. In addition, however, it may be noted that W Wu et al. (*Org. Lett.*, 18, 2938-2941 (2016)) illustrate a further strategy for constructing such ligands, wherein —Z— is methylene and $N^x$ is a substituted oxazolyl by reacting a primary amine of formula $R^1(R^2)PFc$-CH(Me)-$NH_2$ with a variety of substituted chloromethyloxazoles. It will be readily understood that both the —Z— and $N^x$ moieties may be varied according to such a synthetic strategy.

From the discussion herein, it will be appreciated that there is no particular limitation on the architecture of the nitrogen-containing heteroaryl moiety —$N^x$ in the complex of formula (I). This notwithstanding, the nitrogen atom of —$N^x$ is within a heteroaryl ring, which is optionally substituted one or more times with a second electron donating group. According to particular embodiments, the second electron donating group is any one or a combination of substituents selected from the group consisting of amino, $C_{1-6}$alkyl, $C_{1-6}$alkyloxy, hydroxy and amido. Often, the second electron donating group is any one or a combination selected from the group consisting of amino and $C_{1-6}$alkyl. According to particular embodiments, the second electron donating group is an amino, often a tertiary amino substituted with two $C_{1-6}$alkyl substitutents (—$N(C_{1-6}alkyl)_2$). Typically, the tertiary amino is substituted with two of the same $C_{1-6}$alkyl substitutents, selected from the group consisting of methyl, ethyl, propyl, iso-propyl, n-butyl, sec-butyl, isobutyl and tert-butyl. Often, the tertiary amino is dimethylamino.

According to some embodiments, the heterocyclyl ring comprising $N^x$ is an optionally substituted pyridyl, indolyl, quinolinyl, isoquinolinyl, pyrimidinyl, pyrrolyl, pyrrolidinyl, pyrrolinyl, oxazolyl, isooxazolyl, imidazolyl, pyrazolyl, quinoxalinyl, pyridazinyl, triazolyl, triazinyl, imidazolidinyl or oxadiazolyl ring, for example a pyridyl, indolyl, quinolinyl, isoquinolinyl, pyrimidinyl, pyrrolyl, oxazolyl, isooxazolyl, imidazolyl, pyrazolyl, quinoxalinyl, pyridazinyl, or triazolyl ring; and/or a monocyclic heteroaryl ring. According to particular embodiments, the heterocyclyl ring comprising $N^x$ is an optionally substituted pyridyl ring, for example a pyridyl ring optionally substituted one or more times with an amino substituent, which is substituted with Z at a carbon atom adjacent to the nitrogen atom of the pyridyl ring. Typically, $N^x$ is a pyridyl ring substituted with an electron donating group at the 4-position and substituted with Z at a carbon atom adjacent to the nitrogen atom of the pyridyl ring. According to still more particular embodiments, —$N^x$ is 4-dimethylaminopyridin-2yl or 2-pyridyl.

At least one of $R^1$, $R^2$ and —$N^x$ is substituted one or more times with the first and/or second electron donating group, respectively. If at least one of $R^1$ and $R^2$ is substituted with one or more first electron donating groups then —$N^x$ may be unsubstituted. If —$N^x$ is substituted with one or more second electron donating groups then $R^1$ and/or $R^2$ may be unsubstituted. Sometimes, $R^1$ and $R^2$ are substituted one or more times with a first electron donating group. Sometimes, $R^1$ and $R^2$ are substituted one or more times with a first electron donating group and —$N^x$ is substituted one or more times with a second electron donating group.

As well as the tridentate ligand of formula $R^1(R^2)PFc$-CH(Me)-NH—Z—$N^x$, within the complexes of formula (I), the complex additionally comprises the ligands $L^1$-$L^3$. These may constitute one, two or three ligands depending on whether one of them is a bidentate or a tridentate ligand: each of $L^1$-$L^3$ independently may represent a monodentate neutral or anionic ligand; one of $L^1$-$L^3$ may represent a monodentate neutral or anionic ligand and the other two of $L^1$-$L^3$ together represent a bidentate neutral or anionic ligand; or $L^1$-$L^3$ together may represent a tridentate neutral or anionic ligand.

The nature of the $L^1$-$L^3$ ligands is not of particular significance to the present invention: any convenient neutral or anionic ligands may be used, which may be monodentate, bidentate or tridentate, typically monodentate or bidentate. The ligands $L^1$-$L^3$ may be, for example, selected from the group consisting of (i) neutral ligands selected from the group consisting of carbon monoxide, nitrogen monoxide, amines, ethers, thioethers, sulfoxides, nitriles, for example acetonitrile, isocyanides, for example methyl isocyanide, phosphorus-containing ligands based on either phosphorus (Ill) or phosphorus (V) and water; and (ii) anionic ligands selected from the group consisting of halides, alkoxides, anions of carboxylic, sulfonic and phosphoric acids, amido ligands, thiolates, phosphides, cyanide, thiocyanate, isothiocyanate, and enolate ions, for example acetylacetonate. Where $L^1$-$L^3$ together represent a tridentate ligand, this is often, but not necessarily neutral. An example of a neutral tridentate ligand is diglyme.

According to particular embodiments of this invention $L^1$-$L^3$ constitute three ligands selected from neutral monodentate ligands. According to these and other embodiments, $L^1$-$L^3$ may be the same. For example, $L^1$-$L^3$ may constitute three carbon monoxide ligands.

Where the complex of formula (I) is charged, the catalyst comprises one or more additional counterions to balance the charge of the complex, i.e. the charge resultant from the complex formed by the manganese centre Mn, and the ligand or ligands $L^1$-$L^3$ and $R^1(R^2)$PFc-CH(Me)-NH—Z—$N^x$. As with the ligand or ligands $L^1$-$L^3$, the nature of any such additional counterions is not of particular importance to the working of the present invention. Where these are present, they may be, for example, selected from the group consisting of halides, tetraarylborates, $SbF_6^-$, $SbCl_6^-$, $AsF_6^-$, $BF_4^-$, $PF_6^-$, $ClO_4^-$ and $CF_3SO_3^-$, optionally wherein the tetraarylborate ligands are selected from the group consisting of $[B\{3,5$-$(CF_3)_2C_6H_3\}_4]^-$, $[B\{3,5$-$(CH_3)_2C_6H_3\}_4]^-$, $[B(C_6F_5)_4]^-$ and $[B(C_6H_5)_4]^-$, for example where the tetraarylborate ligand is $[B\{3,5$-$(CF_3)_2C_6H_3\}_4]^-$, which is known as tetrakis(3,5-bis(trifluoromethyl)phenyl) borate (BARF)).

According to particular embodiments of the invention, the complex has a single positive charge (for example resultant from the manganese centre being a manganese ion in oxidation state (I) and the ligand or ligands $L^1$-$L^3$ being three neutral monodentate ligands, for example three carbon monoxide ligands) and the catalyst further comprises one halide or tetrarylborate counteranion. According to still more particular embodiments of such catalysts, the counteranion is bromide or BARF. Often, the counterion is a halide, typically bromide.

As will be recognised, the complexes of formula (I) exhibit chirality, both on account of the stereogenic centre adjacent to the Fc moiety (which bears the methyl group depicted within the compounds of formula (I)), and also on account of the planar chirality resultant from the 1,2-connectivity to the remainder of the complex of formula (I), from one of the two cyclopentadienyl rings of the Fc moiety. As has also been alluded to, however, if control of the enantiomeric excess of the optically active alcohol provided by hydrogenation is not desirable, it will be understood that the invention may be operated using catalysts comprising mixtures of any stereoisomers (for example enantiomers or diastereomers) of complexes of formula (I), for example racemic mixtures of enantiomeric complexes and catalysts comprising these.

For example, according to particular embodiments of the invention, the catalyst has one of the formulae:

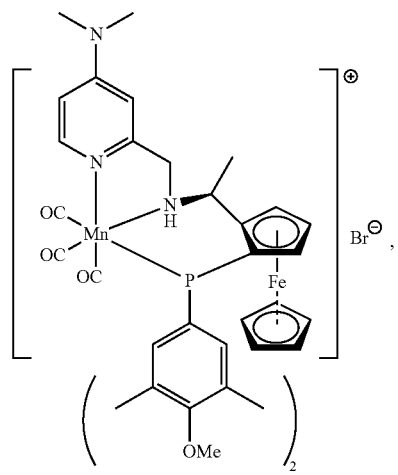

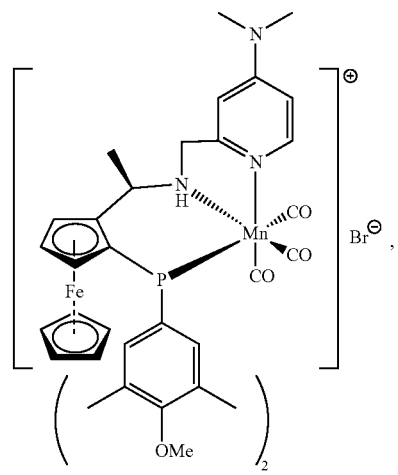

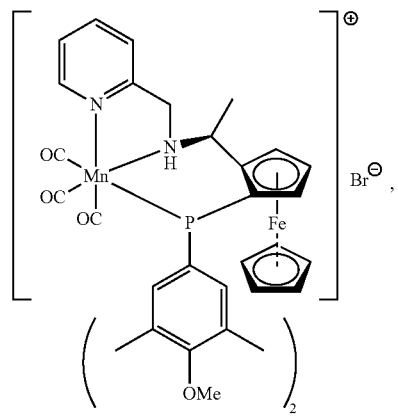

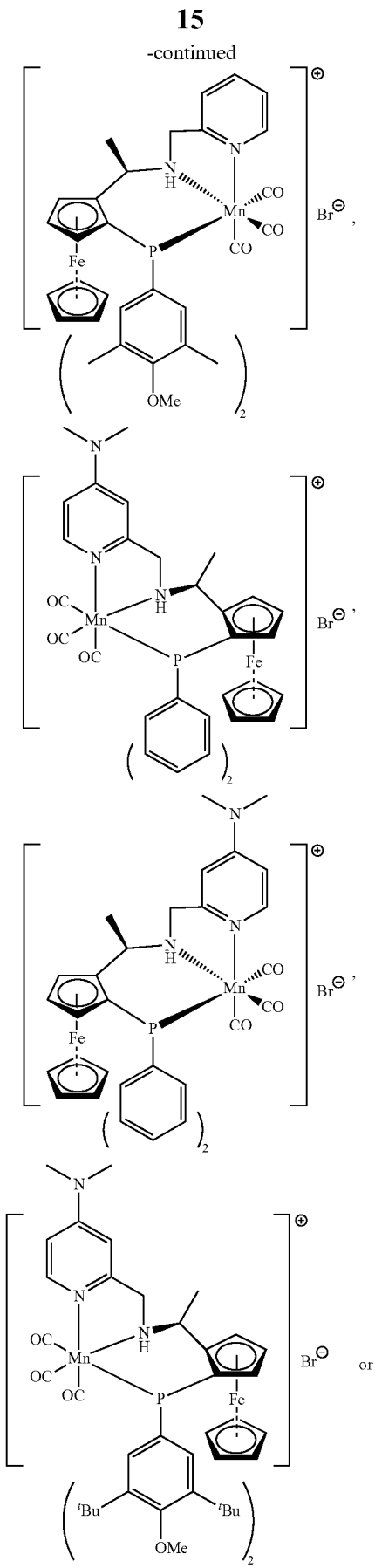
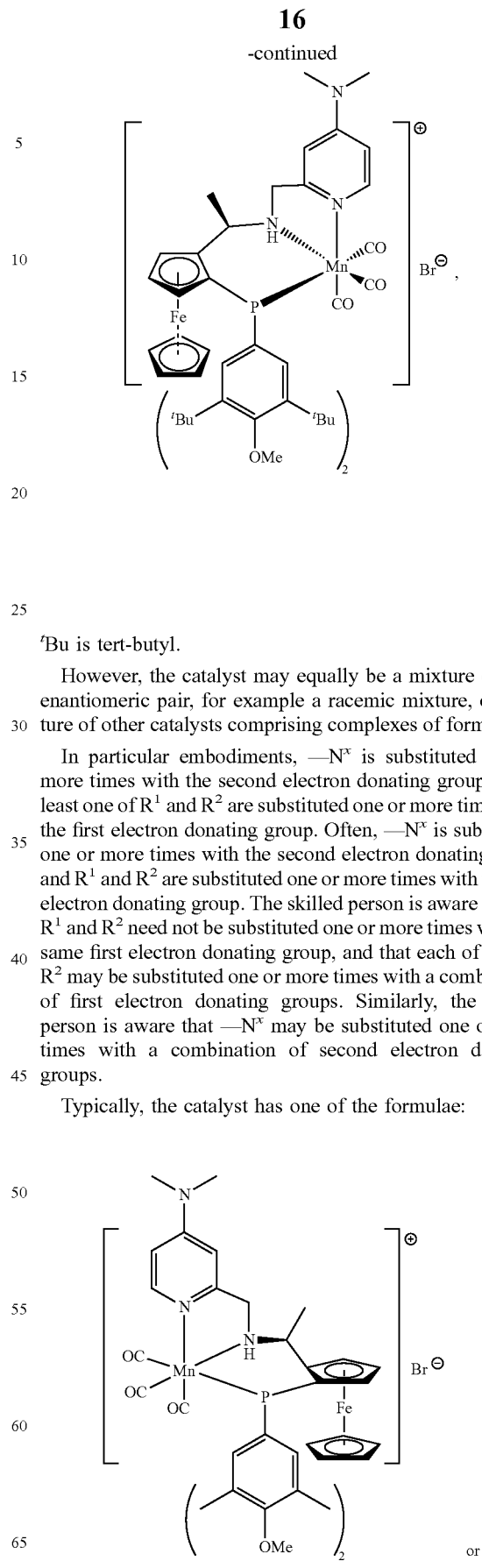

${}^t$Bu is tert-butyl.

However, the catalyst may equally be a mixture of each enantiomeric pair, for example a racemic mixture, or mixture of other catalysts comprising complexes of formula (I).

In particular embodiments, —N$^x$ is substituted one or more times with the second electron donating group and at least one of R$^1$ and R$^2$ are substituted one or more times with the first electron donating group. Often, —N$^x$ is substituted one or more times with the second electron donating group and R$^1$ and R$^2$ are substituted one or more times with the first electron donating group. The skilled person is aware that the R$^1$ and R$^2$ need not be substituted one or more times with the same first electron donating group, and that each of R$^1$ and R$^2$ may be substituted one or more times with a combination of first electron donating groups. Similarly, the skilled person is aware that —N$^x$ may be substituted one or more times with a combination of second electron donating groups.

Typically, the catalyst has one of the formulae:

-continued

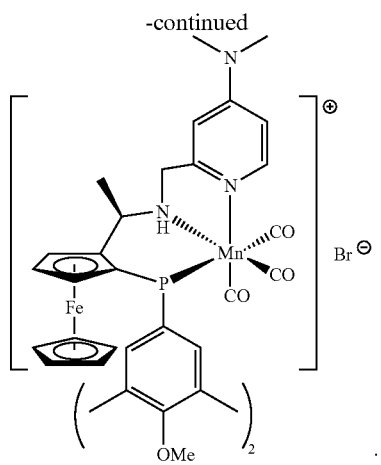

As already alluded to above, catalysts useful in connection with the present invention can, for example, be prepared by mixing an appropriate manganese salt, which may or may not comprise the ligand or ligands $L^1$-$L^3$, and additional ligand(s), e.g. a ligand of the formula $R^1(R^2)$PFc-CH(Me)-NH—Z—$N^x$, suitable to form a catalyst comprising a complex of formula (I), in the same reaction vessel in which a hydrogenation of the present invention is conducted. Alternatively, an optionally well-defined catalyst may be prepared ex situ, as briefly described above. It is readily within the ability of those of normal skill in the art to prepare such catalysts, using the guidance herein, including with reference to the experimental section and prior art with which the skilled person is aware, including that cited herein.

It will be readily appreciated by those skilled in the art that, if desired, recognised methods of immobilisation of catalysts of formula (I) herein can be used to generate heterogeneous catalysts, for example by absorption onto a suitable solid support or reacted with such a support to form a covalently bound ligand or catalyst.

A characteristic feature of the method of the present invention involves the use of a base. Often, the base is selected from the group consisting of potassium carbonate, potassium phosphate, potassium hydroxide, potassium tert-butoxide, sodium tert-butoxide, sodium carbonate, cesium carbonate, sodium hydroxide, lithium carbonate, lithium hydroxide, calcium hydroxide, potassium bicarbonate, sodium bicarbonate, sodium methoxide, lithium bicarbonate and tertiary amines.

We have found that use of the manganese-based catalysts described herein permits hydrogenation of ketones to be effected at a variety of temperatures and with a variety of solvents, but without the need to use a very strong base (in particular a metal alkoxide such as sodium methoxide, sodium tert-butoxide and potassium tert-butoxide). The weaker bases that may be employed in the hydrogenation method disclosed herein (for example, potassium carbonate) are typically cheaper, easier to use and environmentally friendly.

According to some embodiments of the invention, the base is selected from the group consisting of a lithium, beryllium, sodium, magnesium, potassium, calcium or cesium carbonate, phosphate, hydroxide or bicarbonate (i.e one of these four salts of these six metals) or a mixture thereof, e.g. is selected from the group consisting of a lithium, sodium, magnesium, potassium, calcium or cesium carbonate, phosphate, hydroxide or bicarbonate, or a mixture thereof. According to more specific embodiments of the invention (i.e. in accordance with both the first and second aspects), the base is selected from the group consisting of potassium carbonate, potassium phosphate, potassium hydroxide, sodium carbonate, cesium carbonate, sodium hydroxide, lithium carbonate, lithium hydroxide, calcium hydroxide, potassium bicarbonate, sodium bicarbonate and lithium bicarbonate.

According to particular embodiments of the invention, the conjugate acid of the base has a pKa from 10.3 to 14. Such pKas exclude, for example, bicarbonates.

The skilled person will recognise that extensive conversion of ketone to alcohol via hydrogenation with a metal bicarbonate base may be increased by routine modifications of reaction protocols, for example by increasing the concentrations of such bases, catalyst loading, hydrogen pressure, temperature, duration of reaction or any combination of these modifications.

According to still more particular embodiments of the invention, the base is selected from the group consisting of potassium carbonate, potassium phosphate, potassium hydroxide, sodium carbonate, cesium carbonate, sodium hydroxide, lithium carbonate, lithium hydroxide, and calcium hydroxide, for example the group consisting of potassium carbonate, potassium phosphate, potassium hydroxide, sodium carbonate and cesium carbonate.

According to other embodiments of the invention, the base used in accordance with these methods of hydrogenation may be a tertiary amine, typically of the formula $N(C_{1-6}alkyl)_3$, in which each alkyl group need not necessarily be the same. Examples of tertiary amines that may be used include triethylamine, N,N-dimethylamine and N,N-diisopropylethylamine (also known as Hunig's base).

According to some embodiments, the invention provides a method comprising hydrogenating a ketone in the presence of (i) a base, which is a lithium, beryllium, sodium, magnesium, potassium, calcium or cesium carbonate, phosphate, hydroxide or bicarbonate, or a tertiary amine, for example of the formula $N(C_{1-6}alkyl)_3$ defined above (ii) hydrogen gas and (iii) a catalyst comprising a charged or neutral complex of formula (I) as defined in connection with the first aspect of the invention, and elsewhere herein.

According to particular embodiments of the invention, the base is selected from the group consisting of potassium carbonate, potassium phosphate, potassium hydroxide, sodium carbonate, cesium carbonate, sodium hydroxide, lithium carbonate, lithium hydroxide, calcium hydroxide, potassium bicarbonate, sodium bicarbonate and lithium bicarbonate, for example wherein the base is selected from the group consisting of potassium carbonate, potassium phosphate, potassium hydroxide, sodium carbonate, cesium carbonate, sodium hydroxide, lithium carbonate, lithium hydroxide, and calcium hydroxide, and, according to particular embodiments, wherein the base is selected from the group consisting of potassium carbonate, potassium phosphate, potassium hydroxide, sodium carbonate and cesium carbonate.

The methods of the invention, as is typical for hydrogenation reactions, are conducted in the presence of hydrogen gas, under pressure. Generally the pressure at which the reactions are conducted is in the range of about 1 bar (100 kPa) to about 100 bar (10,000 kPa), for example from about 20 bar (2,000 kPa) to about 80 bar (8,000 kPa), although higher or lower pressures may on occasion be convenient.

The reactions may be carried out in any convenient solvent as may be suitable for the substrate for the reaction (i.e. the ketone). In certain embodiments, it may be convenient to conduct hydrogenations in the absence of solvent.

Any of the commonly encountered solvents in organic chemistry can potentially be utilised.

As already alluded to above, we have found that, in contrast with their unsubstituted analogues, the manganese-based compounds described herein dissolve readily in a variety of solvents, allowing a greater flexibility in the choice of solvent to use when working with the compounds of the invention.

Typical solvents for use in the present invention include simple alcohols, such as $C_{1-10}$hydrocarbyl alcohols, often saturated aliphatic $C_{2-8}$alcohols, for example, ethanol, isopropanol and tert-butanol; polyvalent alcohols such as ethylene glycol, propylene glycol, 1,2-propanediol and glycerol; ethers, for example tetrahydrofuran (THF) 1,4-dioxane, methyl tert-butyl ether, cyclopentyl methyl ether; aliphatic and aromatic hydrocarbon solvents, for example $C_{5-12}$alkanes, benzene, toluene and xylene and halogenated (typically chlorinated) hydrocarbon solvents, for example dichloromethane and chlorobenzene, or mixtures thereof, in particular, mixtures of alcohols, for example ethanol or isopropanol, and hydrocarbon solvents such as hexanes, xylenes (i.e. isomeric mixtures) or toluene. According to particular embodiments, methanol is not used as a solvent in the present invention.

Conveniently, however, hydrogenation reactions of the present invention can typically be conducted in $C_{1-10}$hydrocarbyl alcohols alone (i.e. in which the only solvent is the alcohol, or there is minimal (e.g. less than 5 vol %, more typically less than 2 vol %) contamination with other liquid, for example water), in particular in ethanol or isopropanol. According to some embodiments of the invention, therefore the solvent for the reaction is isopropanol. According to other embodiments, the solvent is ethanol.

It will be understood that the precise conditions for any given hydrogenation reaction may be varied within the routine ability of those of normal skill in the art. Thus, the concentration of catalyst and hydrogen pressure may typically be varied within the ranges already discussed. Operating temperatures that may be used typically vary from about −20° C. to about 200° C., often from about 10° C. to about 120° C., for example from about 30° C. to about 110° C., typically from about 30 to about 80° C.; and durations of reaction may vary from about 5 minutes to about 36 hours, for example from about 1 hour to about 24 hours or from about 2 hours to about 18 hours.

Suitable amounts of base that may be used can likewise be determined by the skilled person. One of the advantages of the present invention is that the costs of many of the bases are significantly lower than those of metal alkoxides. Another advantage is the greatly reduced sensitivity of the bases described herein to water. The use of larger amounts of bases in connection with the present invention is therefore less problematic than with metal alkoxides. Examples of suitable amounts of base to use may vary from about 0.1 mol % to about 1000 mol %, with respect to the ketone reactant, for example from about 1 mol % to about 100 mol %, e.g. from about 2 to about 50 mol %. It may on occasion be convenient or advantageous to use greater quantities of base, however, for example up to 2000 mol % or more. Combinations of more than one base may also be used.

As noted above, the present invention is premised, in part, on the ability to effect hydrogenation of ketones at a variety of temperatures and with a variety of solvents. Ketones that may therefore serve as the substrate for the hydrogenation reactions in accordance with the present invention are therefore not particularly limited. Typically, however, the ketone functionality is connected to one or more hydrocarbyl moieties (for the avoidance of doubt, ketones that may be hydrogenated in accordance with the scope of the present invention include cyclic ketones (for example cyclohexanone), optionally comprising amino or halo functionality. According to particular embodiments, the hydrocarbyl moieties to which the ketone functional group is connected do not comprise an unsaturated aliphatic portion, although they may comprise aromatic or heteroaromatic moieties in addition to one or more saturated aliphatic portions.

According to particular embodiments of the present invention, the ketone is pro-chiral. When hydrogenating pro-chiral ketones in accordance with the present invention, optically active alcohols result. The enantiomeric excess of such alcohols may be controlled through the use of the catalysts disclosed herein, in non-racemic forms. In some embodiments of the invention, an optically active alcohol is provided by the method of the invention with an enantiomeric excess (e.e.) of about 40% to about 100%, about 50% to about 90%, about 60% to about 90%, about 50% to about 80%, or about 60% to about 80%. Typically, the enantiomeric excess is about 50 to about 90%.

Viewed from a second aspect, the invention provides a catalyst comprising a charged or neutral complex of formula (I) as defined in the first aspect, wherein —$N^x$ is substituted one or more times with the second electron donating group and at least one of $R^1$ and $R^2$ are substituted one or more times with the first electron donating group.

Viewed from a third aspect, the invention provides a compound comprising a charged or neutral complex of formula (I) as defined in the first aspect, wherein —$N^x$ is substituted one or more times with the second electron donating group and at least one of $R^1$ and $R^2$ are substituted one or more times with the first electron donating group.

For the avoidance of doubt, the embodiments relevant to formula (I) of the first aspect of the invention are also relevant to formula (I) of the second and third aspects of the invention. For example, in some embodiments of the second and third aspects, —$N^x$ is a pyridyl ring substituted one or more times with the second electron donating group and $R^1$ and $R^2$ are each phenyl moieties optionally substituted one or more times with the first electron donating group, with the proviso that at least one of $R^1$ and $R^2$ are substituted one or more times with the first electron donating group.

In particular embodiments of the second and third aspects of the invention, —$N^x$ is substituted one or more times with the second electron donating group and $R^1$ and $R^2$ are substituted one or more times with the first electron donating group. For example, —$N^x$ may be a pyridyl ring substituted one or more times with the second electron donating group and $R^1$ and $R^2$ may each be phenyl moieties substituted one or more times with the first electron donating group.

Any solvates of the catalysts and compounds of the second and third aspects of the invention, lie within the ambit of the invention. The skilled person is aware of suitable processes for the formation of solvates, hemisolvates, hydrates and the like. Amorphous and crystalline forms of the catalysts and compounds of formula (I) also fall within the scope of the invention. Furthermore, compositions comprising the catalysts and compounds of formula (I), optionally as solvates, in combination with one or more excipients lie within the scope of the invention.

Each and every patent and non-patent reference referred to herein is hereby incorporated by reference in its entirety, as if the entire contents of each reference were set forth herein in its entirety.

The aspects and embodiments of the invention are further described in the following clauses:

1. A method comprising hydrogenating a ketone in the presence of (i) a base, (ii) hydrogen gas and (iii) a catalyst comprising a charged or neutral complex of formula (I):

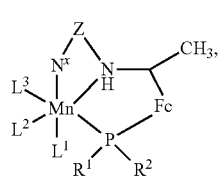

(I)

wherein:
Mn is a manganese atom or a manganese ion in oxidation state (I) to (VII);
$R^1$ and $R^2$ are each independently $C_{4-8}$monocyclic aryl or $C_{3-7}$monocyclic heteroaryl moieties, optionally substituted one or more times with a first electron donating group;
-Fc- denotes a ferrocene (bis($\eta^5$-cyclopentadienyl)iron) moiety covalently bonded via adjacent carbon atoms of one of the two cyclopentadienyl moieties, and which may be optionally further substituted, in either cyclopentadienyl ring, one or more times with a substituent selected from the group consisting of halo, aliphatic $C_{1-6}$hydrocarbyl, trihalomethyl, aryl, heteroaryl, hydroxy, nitro, amino, alkoxy, alkylthio, carboxylate, sulfonate, phosphate, cyano, thio, formyl, ester, acyl, thioacyl, carbamido and sulfonamido;
—Z— is an alkylene linker of the formula —$(CH_2)_{1-6}$— in which one or more of the hydrogen atoms of the alkylene may be independently substituted with an alkyl, aryl, heteroaryl, hydroxy, nitro, amino, alkoxy, alkylthio or thiol substituent;
—$N^x$ is a nitrogen-containing heteroaryl moiety, optionally substituted one or more times with a second electron donating group, with the proviso that at least one of $R^1$, $R^2$ and —$N^x$ is substituted one or more times with the first and/or second electron donating group respectively; and
$L^1$-$L^3$ constitute one, two or three ligands in which each of $L^1$-$L^3$ independently represents a monodentate neutral or anionic ligand; or one of $L^1$-$L^3$ represents a monodentate neutral or anionic ligand and the other two of $L^1$-$L^3$ together represent a bidentate neutral or anionic ligand; or $L^1$-$L^3$ together represent a tridentate neutral or anionic ligand,
wherein, when the complex of formula (I) is charged, the catalyst comprises one or more additional counterions to balance the charge of the complex.

2. The method of clause 1 wherein the base is selected from the group consisting of potassium carbonate, potassium phosphate, potassium hydroxide, potassium tert-butoxide, sodium tert-butoxide, sodium carbonate, cesium carbonate, sodium hydroxide, lithium carbonate, lithium hydroxide, calcium hydroxide, potassium bicarbonate, sodium bicarbonate, lithium bicarbonate, sodium methoxide and tertiary amines.

3. The method of clause 1 or clause 2 wherein the conjugate acid of the base has a pKa from 6.3 to 14.

4. The method of clause 3 wherein the base is selected from the group consisting of potassium carbonate, potassium phosphate, potassium hydroxide, sodium carbonate, cesium carbonate, sodium hydroxide, lithium carbonate, lithium hydroxide, and calcium hydroxide.

5. The method of clause 4 wherein the base is selected from the group consisting of potassium carbonate, potassium phosphate, potassium hydroxide, sodium carbonate and cesium carbonate.

6. The method of any one of clauses 1 to 5 wherein Mn is a manganese ion in oxidation state (I) or (II).

7. The method of any one of clauses 1 to 5 wherein the manganese ion is in oxidation state (I).

8. The method of any one of clauses 1 to 7 wherein $R^1$ and $R^2$ are each independently optionally substituted $C_{4-6}$monocyclic aryl or $C_{3-5}$monocyclic heteroaryl moieties.

9. The method of clause 8 wherein $R^1$ and $R^2$ are each optionally substituted phenyl, or furanyl moieties.

10. The method of any one of clauses 1 to 9 wherein the first electron donating group is any one or a combination selected from the group consisting of $C_{1-6}$alkyl and $C_{1-6}$alkoxy.

11. The method of clause 10 wherein the $C_{1-6}$alkyl is selected from any one of the group consisting of methyl, ethyl, isopropyl and tert-butyl.

12. The method of clause 10 or 11 wherein the $C_{1-6}$alkoxy is selected from any one of the group consisting of methoxy, ethoxy, isopropoxy and tert-butoxy.

13. The method of any one of clauses 1 to 12 wherein $R^1$ and $R^2$ are the same.

14. The method of any one of clauses 1 to 7 wherein $R^1$ and $R^2$ are both 4-methoxy-3,5-dimethylphenyl, 4-methoxy-3,5-di-tert-butylphenyl or phenyl.

15. The method of any one of clauses 1 to 14 wherein, in addition to the ferrocene's points of connectivity to the remainder of the complex of formula (I), one or more carbon atoms of either cyclopentadienyl ring of the ferrocene moiety are independently optionally substituted with halo or $C_{1-6}$alkyl substituents.

16. The method of any one of clauses 1 to 15 wherein neither cyclopentadienyl ring of the ferrocene moiety is substituted other than through the ferrocene's points of connectivity with the remainder of the complex of formula (I).

17. The method of any one of clauses 1 to 16 wherein —Z— is of the formula —$(CH_2)$—, —$(CHR^3)$— or —$(CH_2)_2$—, wherein $R^3$ is the alkyl, aryl, heteroaryl, hydroxy, nitro, amino, alkoxy, alkylthio or thiol substituent.

18. The method of clause 17 wherein —Z— is of the formula —$(CH_2)$—, —$(CHR^3)$— or —$(CH_2)_2$—, wherein $R^3$ is an $C_{1-6}$alkyl substituent or phenyl optionally substituted one or more times with $C_{1-6}$alkyl and/or halo.

19. The method of clause 18 wherein —Z— is of the formula —$(CH_2)$—, —$(CHR^3)$— or —$(CH_2)_2$—, wherein $R^3$ is methyl or phenyl optionally substituted one or more times with $C_{1-6}$alkyl and/or halo.

20. The method of any one of clauses 1 to 19 wherein —Z— is unsubstituted.

21. The method of clause 20 wherein —Z— is of the formula —$(CH_2)$— or —$(CH_2)_2$—.

22. The method of clause 21 wherein —Z— is of the formula —$(CH_2)$—.

23. The method of any one of clauses 1 to 7 wherein the $R^1R^2P$-Fc-CH(Me)-NH-component of the complex is 1-[bis(4-methoxy-3,5-dimethylphenyl)phosphino]-2-[1-(HN)ethyl]ferrocene, 1-[bis(4-methoxy-3,5-di-tert-butylphenyl)phosphino]-2-[1-(HN)ethyl]ferrocene or 1-[1-(HN)ethyl]-2-(diphenylphosphino)ferrocene.

24. The method of clause 23, wherein the $R^1R^2P$-Fc-CH(Me)-NH— component of the complex is (S)-1-[bis(4-methoxy-3,5-dimethylphenyl)phosphino]-2-[(R)-1-(HN)ethyl]ferrocene, (R)-1-[bis(4-methoxy-3,5-dimethylphenyl)phosphino]-2-[(S)-1-(HN)ethyl]ferrocene or a mixture thereof; (S)-1-[bis(4-methoxy-3,5-di-tert-butylphenyl)phosphino]-2-[(R)-1-(HN)ethyl]ferrocene, (R)-1-[bis(4-methoxy-3,5-di-tert-butylphenyl)phosphino]-2-[(S)-1-(HN)ethyl]ferrocene or a mixture thereof; (S)-1-[(R)-1-(HN)ethyl]-2-(diphenylphosphino)ferrocene, (R)-1-[(S)-1-(HN)ethyl]-2-(diphenylphosphino)ferrocene or a mixture thereof.

25. The method of any one of clauses 1 to 24 wherein the second electron donating group is any one or a combination selected from the group consisting of amino, $C_{1-6}$alkyl, $C_{1-6}$alkyloxy, hydroxy and amido.

26. The method of clause 25, wherein the second electron donating group is any one or a combination selected from the group consisting of amino and $C_{1-6}$alkyl.

27. The method of clause 26, wherein the second electron donating group is an amino.

28. The method of clause 27, wherein the amino is a tertiary amino, substituted with two $C_{1-6}$alkyl substituents.

29. The method of clause 28, wherein the two $C_{1-6}$alkyl substituents are the same and are selected from the group consisting of methyl, ethyl, propyl, iso-propyl, n-butyl, sec-butyl, isobutyl and tert-butyl.

30. The method of any one of clauses 1 to 29 wherein —$N^x$ is an optionally substituted pyridyl, indolyl, quinolinyl, isoquinolinyl, pyrimidinyl, pyrrolyl, pyrrolidinyl, pyrrolinyl, oxazolyl, isooxazolyl, imidazolyl, pyrazolyl, quinoxalinyl, pyridazinyl, triazolyl, triazinyl, imidazolidinyl or oxadiazolyl ring.

31. The method of clause 30, wherein —$N^x$ is an optionally substituted pyridyl, indolyl, quinolinyl, isoquinolinyl, pyrimidinyl, pyrrolyl, oxazolyl, isooxazolyl, imidazolyl, pyrazolyl, quinoxalinyl, pyridazinyl, or triazolyl ring.

32. The method of clause 31, wherein —$N^x$ is an optionally substituted monocyclic heteroaryl ring.

33. The method of any one of clauses 1 to 32 wherein —$N^x$ is an optionally substituted pyridyl ring.

34. The method of clause 33, wherein —$N^x$ is a pyridyl ring, optionally substituted with a tertiary amino at the 4-position.

35. The method of clause 34, wherein —$N^x$ is a 4-dimethylamino pyridyl ring or a pyridyl ring, which is substituted with Z at a carbon atom adjacent to the ring nitrogen atom of the pyridyl ring.

36. The method of clause 35, wherein —$N^x$ is 4-dimethylaminopyridin-2-yl or 2-pyridyl.

37. The method of any one of clauses 1 to 36 wherein each of the one, two or three ligands $L^1$-$L^3$ is selected from the group consisting of (i) neutral ligands selected from the group consisting of carbon monoxide, nitrogen monoxide, amines, ethers, thioethers, sulfoxides, nitriles (RCN), isocyanide (RNC), phosphorus-containing ligands based on either phosphorus (III) or phosphorus (V) and water; and (ii) anionic ligands selected from the group consisting of halides, alkoxides, anions of carboxylic, sulfonic and phosphoric acids, amido ligands, thiolates, phosphides, cyanide, thiocyanate, isothiocyanate and enolate ions.

38. The method of clause 37 wherein $L^1$-$L^3$ constitute three ligands selected from neutral monodentate ligands.

39. The method of clause 38 wherein each of $L^1$-$L^3$ is the same.

40. The method of clause 39 wherein each of $L^1$-$L^3$ is carbon monoxide.

41. The method of any one of clauses 1 to 40 wherein, when the catalyst comprises one or more additional counterions, these are selected from the group consisting of halides, tetraarylborates, $SbF_6^-$, $SbCl_6^-$, $AsF_6^-$, $BF_4^-$, $PF_6^-$, $ClO_4^-$ and $CF_3SO_3^-$.

42. The method of clause 41 wherein the additional counterions are selected from the group consisting of halides, $SbF_6^-$, $SbCl_6^-$, $AsF_6^-$, $BF_4^-$, $PF_6^-$, $ClO_4^-$, $CF_3SO_3^-$, $[B\{3,5\text{-}(CF_3)_2C_6H_3\}_4]^-$, $[B\{3,5\text{-}(CH_3)_2C_6H_3\}_4]^-$, $[B(C_6F_5)_4]^-$ and $[B(C_6H_5)_4]^-$.

43. The method of clause 42, wherein the complex has a single positive charge and catalyst further comprises one halide or tetrarylborate counteranion.

44. The method of clause 43, wherein the counteranion is bromide or $[B\{3,5\text{-}(CF_3)_2C_6H_3\}_4]^-$.

45. The method of any one of clauses 41 to 44, wherein the counterion is a halide.

46. The method of any one of clauses 1 to 5, wherein the catalyst has any one of the formulae:

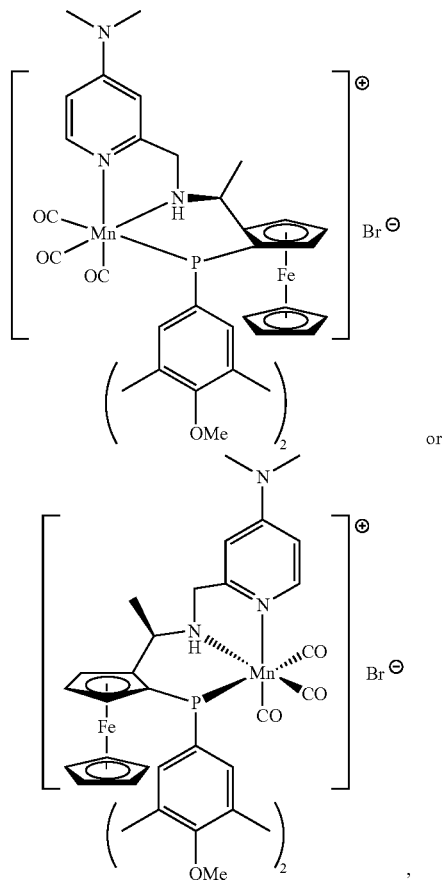

or is a mixture thereof;

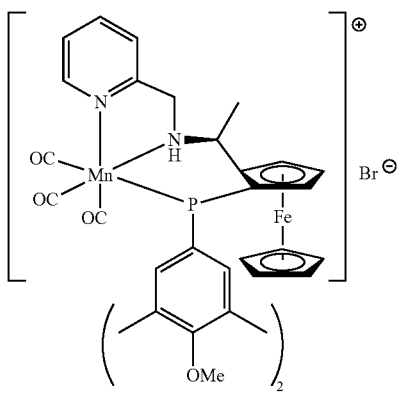

or

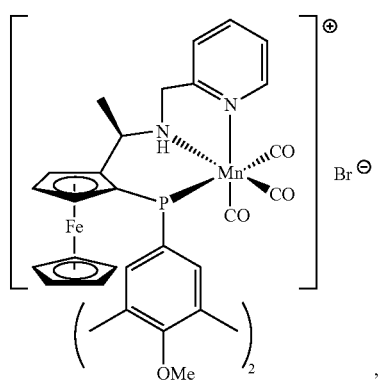

or is a mixture thereof;

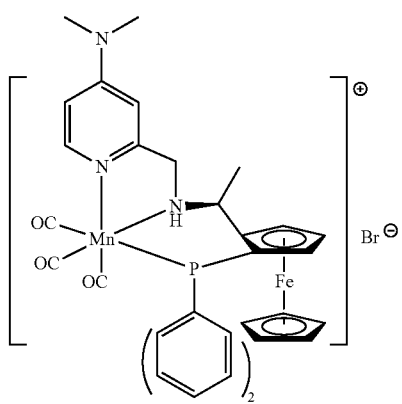

or

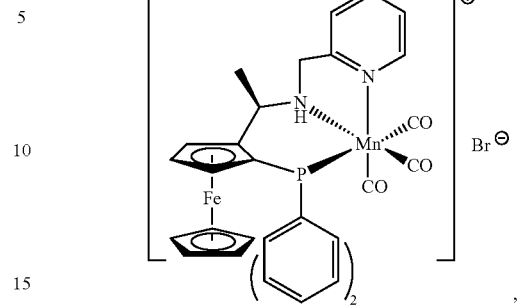

or is a mixture thereof;

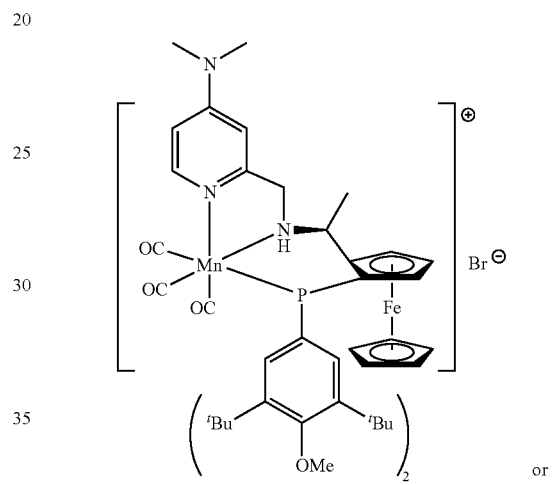

or

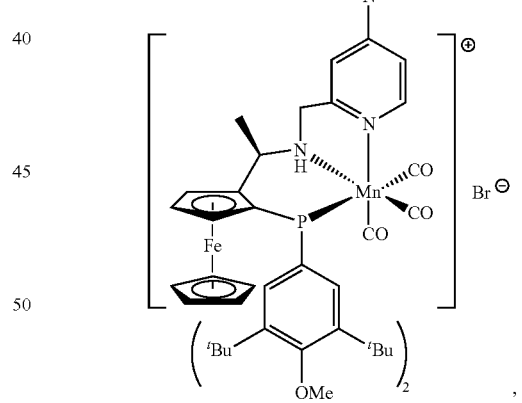

or is a mixture thereof;

47. The method of any one of clauses 1 to 46 wherein —$N^x$ is substituted one or more times with the second electron donating group and at least one of $R^1$ and $R^2$ are substituted one or more times with the first electron donating group.

48. The method of any one of clauses 1 to 47 wherein —$N^x$ is substituted one or more times with the second electron donating group and $R^1$ and $R^2$ are substituted one or more times with the first electron donating group.

49. The method of any one of clauses 1 to 5, wherein the catalyst has any one of the formulae:

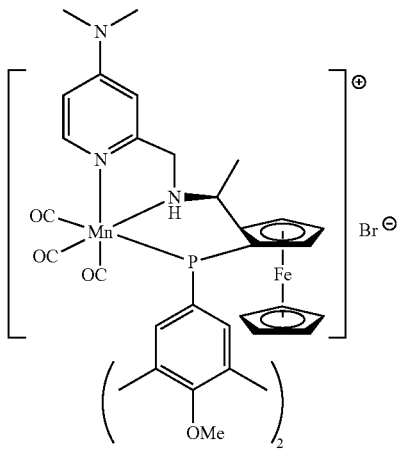

or

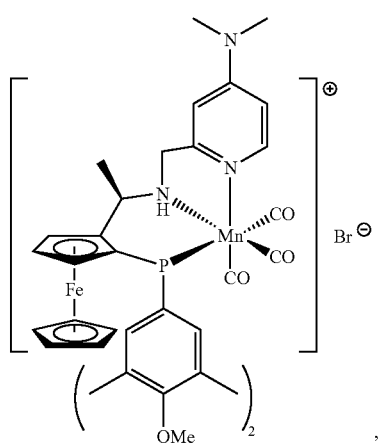

or is a mixture thereof.

50. The method of clause 46 or clause 49 wherein the mixture is a racemic mixture.
51. The method of any one of clauses 1 to 50 wherein the ketone is pro-chiral.
52. The method of clause 51, wherein an optically active alcohol is provided by the hydrogenation with an enantiomeric excess of about 40% to about 100%, about 50% to about 90%, about 60% to about 90%, about 50% to about 80%, or about 60% to about 80%.
53. The method of clause 52, wherein the enantiomeric excess is about 50 to about 90%.
54. A catalyst comprising a charged or neutral complex of formula (I) as defined in any one of clauses 47 to 50.
54. A compound comprising a charged or neutral complex of formula (I) as defined in any one of clauses 47 to 50.

The non-limiting examples below more fully illustrate the embodiments of this invention.

Synthesis of ($R_c,S_p$)—N-2-picolinyl-1-[2-bis(4-methoxy-3,5-dimethylphenyl)-phosphine]-ferrocenylethylamine (1)

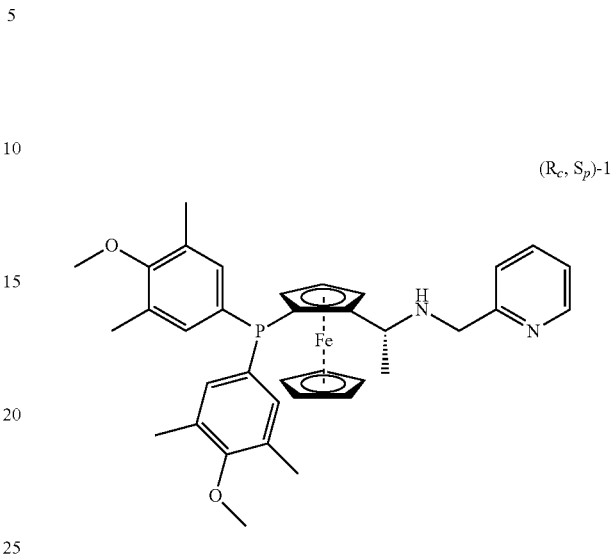

($R_c,S_p$)—N,N-dimethyl-1-[2-bis(4-methoxy-3,5-dimethylphenyl)phosphine]-ferrocenylethylamine (1.0 g, 1.79 mmol, 1.0 equiv.) was added to degassed acetic anhydride (5 mL) and stirred at room temperature for 16 h. The volatiles were removed in vacuo using toluene to azaeotropically remove residual acetic anhydride. The crude material was dissolved in degassed dry methanol (10 mL) and 2-aminomethylpyridine (0.37 mL, 3.59 mmol, 2.0 equiv.) was added. The mixture was refluxed for 4 h then cooled to room temperature and volatiles removed in vacuo. The crude material was added to degassed dichloromethane (10 mL) and degassed saturated aqueous sodium bicarbonate (10 mL). The organic layer was cannulated to a Schlenk flask containing magnesium sulfate. The aqueous layer was extracted with dichloromethane (10 mL) two times, each layer cannulated to the same Schlenk flask as described above. The combined dried organic layer was filtered using a cannula fitted with a filter paper to a round bottom flask and evaporated to dryness. The crude material was purified by column chromatography using dichloromethane/methanol (9/1) to give the target compound as a yellow foam (0.84 g, 1.35 mmol, 76%).

$^1$H-NMR (CDCl$_3$) δ: 8.38 (1H, br d, J=4.8 Hz, C$_{Ar}$H), 7.40 (1H, t, J=7.8 Hz, C$_{Ar}$H), 7.22 (1H, S, C$_{Ar}$H), 7.21 (1H, S, C$_{Ar}$H), 7.02 (1H, t, J=6.7 Hz, C$_{Ar}$H), 6.92 (1H, s, C$_{Ar}$H), 6.90 (1H, S, C$_{Ar}$H), 6.59 (1H, d, J=7.8 Hz, C$_{Ar}$H), 4.54 (1H, m, Fc-H), 4.32 (1H, m, Fc-H), 4.23 (1H, m, —CH—), 4.06 (5H, s, Fc-H), 3.83 (1H, s, Fc-H), 3.77 (3H, m, —OCH$_3$), 3.62 (2H, br s, PyCH$_2$N—), 3.57 (3H, s, —OCH$_3$), 2.31 (6H, s, —CH$_3$), 2.09 (6H, s, —CH$_3$), 1.58 (3H, br s, CHCH$_3$, overlapped with water peak);

$^{31}$P{$^1$H}-NMR (CDCl$_3$) δ: −27.3 ppm;

HRMS: (ES+) calculated for [C$_{36}$H$_{42}$FeN$_2$O$_2$P]$^+$ 621.2328; found 621.2316.

Synthesis of [(R$_c$,S$_p$)—N-2-picolynyl-1-(-2-bis(4-methoxy-3,5-dimethylphenyl)-phosphino)ferrocenyl-ethylamine]-κN$^1$-κN$^2$-κ$^P$-tricarbonyl manganese (I) bromide (2)

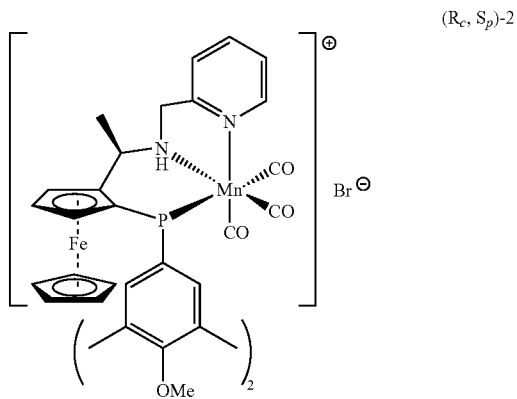

(R$_c$,S$_p$)-2

(R$_c$,S$_p$)—N-2-picolinyl-1-(2-bis(4-methoxy-3,5-dimethylphenyl)phosphine)-ferrocenylethylamine (205 mg, 0.33 mmol, 1.02 equiv.) and bromopentacarbonylmanganese (I) (89 mg, 0.32 mmol, 1.0 equiv.) were stirred in degassed cyclohexane (10 mL) at room temperature under an argon atmosphere. The mixture was refluxed for 16 h under which time an orange slurry formed. The mixture was cooled to room temperature, diluted with $^n$pentane (20 mL), filtered, washed with $^n$pentane (2×20 mL) and dried to give the title compound as a yellow solid (200 mg, 0.26 mmol, 82%). Analysis showed the presence of cyclohexane.

$^1$H-NMR (DCM-d$_2$) δ: 8.60 (1H, br d, J=4.8 Hz, C$_{Ar}$H), 7.65 (1H, S, C$_{Ar}$H), 7.62 (1H, S, C$_{Ar}$H), 7.33 (1H, t, J=6.9 Hz, C$_{Ar}$H), 6.79 (2H, m, C$_{Ar}$H), 6.29 (1H, S, C$_{Ar}$H), 6.28 (1H, s, C$_{Ar}$H), 5.58 (1H, m, —CH—), 4.87 (1H, s, NH), 4.62 (1H, s, Fc-H), 4.48 (1H, s, Fc-H), 4.35 (1H, s, Fc-H), 4.11 (1H, m, PyCH$_2$NH—), 3.85 (5H, s, Fc-H), 3.81 (3H, s, —OCH$_3$), 3.68 (1H, m, PyCH$_2$NH), 3.54 (3H, s, —OCH$_3$), 2.40 (6H, s, —CH$_3$), 1.96 (6H, s, —CH$_3$), 1.70 (3H, br d, J=7.0 Hz, CHCH$_3$), 1.44 (cyclohexane);

$^{13}$C{$^1$H}-NMR (CDCl$_3$) δ: 159.71 (C$_{Ar}$), 158.96 (C$_{Ar}$), 156.65 (C$_{Ar}$), 152.87 (C$_{Ar}$), 135.80 (C$_{Ar}$), 135.02 (C$_{Ar}$), 134.91 (d, J$_{PC}$=11.3 Hz, C$_{Ar}$), 134.20 (C$_{Ar}$), 133.82 (C$_{Ar}$), 131.26 (C$_{Ar}$), 130.93 (d, J$_{PC}$=10.2 Hz, C$_{Ar}$), 130.33 (d, J$_{PC}$=11.3 Hz, C$_{Ar}$), 129.93 (d, J$_{PC}$=10.1 Hz, C$_{Ar}$), 122.31 (C$_{Ar}$), 119.16 (C$_{Ar}$), 91.40 (d, J$_{PC}$=19.3 Hz, Fc-C$^{ipso}$—P), 73.27 (d, J$_{PC}$=28.9 Hz, C$_{Fc}$), 72.84 (C$_{Fc}$), 70.58 (C$_{Fc}$), 69.84 (C$_{Fc}$), 59.70 (OCH$_3$), 59.32 (OCH$_3$), 56.48 (Fc-CH(CH$_3$)—N), 59.27 (C$_{Fc}$), 48.66 (PyCH$_2$), 26.93 (cyclohexane), 20.43 (Fc-CH(CH$_3$)—N), 16.14 (Ar—CH$_3$), 15.54 (Ar—CH$_3$);

$^{31}$P-{$^1$H}-NMR (DCM-d$_2$) δ: +86.8 (s);

IR (ATR): 2927.9 (w), 1924.9 (s), 1845.9 (s), 1473.6 (m), 1217.1 (w), 1111.0 (m), 1008.8 (m), 771.5 (w), 615.3 (m) cm$^-$;

HRMS: (ES+): expected [C$_{39}$H$_{41}$FeMnN$_2$O$_3$P]$^-$: 759.1478, found: 759.1462.

Use of 2 in Ketone Hydrogenation
General Ketone Hydrogenation Procedure

Ketone (1.0 equiv.), manganese catalyst (0.001 equiv.), potassium carbonate (0.05 equiv.) and 1-methylnaphthalene (~50 μL, internal standard) were added to a microwave vial containing a stirring bead. The vial was sealed and evacuated and refilled with argon. This was repeated twice. Degassed ethanol (3.0 mL) was added and the vial septum was pierced with 2×18G needles and placed in a stainless-steel autoclave under an argon atmosphere. The vessel was pressurised with hydrogen gas (50 bar) and vented to the atmosphere. This was repeated twice. The pressure was set to 50 bar using hydrogen gas and the autoclave was sealed and placed in a pre-heated oil bath (50° C.). Stirring was set to 1200 rpm and the reaction was left for 16 h. After the reaction, the vessel was cooled to ambient temperature and vented to the atmosphere, the reaction was analysed by $^1$H-NMR and conversion was estimated using the internal standard (1-methylnaphthalene). The reaction mixture was evaporated to dryness and the crude product was purified by column chromatography as detailed below.

1-phenyl-1-propanol

The product was purified by column chromatography using first hexanes and hexanes/ethyl acetate (1/1) to give the product as a pale-yellow oil. Using 281 mg (2.095 mmol) of propiophenone 250 mg (1.84 mmol) of title compound was isolated (88% yield);

$^1$H-NMR (CDCl$_3$) δ: 7.40-7.28 (5H, m, Ph-H), 4.62 (1H, t, J=6.7 Hz, Ph-CH(OH)—), 1.81 (2H, m, —CH$_2$CH$_3$), 0.95 (3H, t, J=6.1 Hz, —CH$_3$);

$^{13}$C-{$^1$H}-NMR (DEPT) (CDCl$_3$) δ: 144.59 ((C$_{Ar}$—CH(OH)), 128.42 (C$_{Ar}$), 127.52 (C$_{Ar}$), 125.99 (C$_{Ar}$), 76.05 (—CH(OH)—), 31.91 (—CH$_2$), 10.18 (—CH$_3$);

HRMS (EI+): calculated for [C$_{10}$H$_{12}$O]: 136.0888 found: 136.0881.

Chiral analysis was performed using a Chiralcel OD-H column using $^n$hexane/isopropanol (95/5) mobile phase, flow 1.0 mL/min, ee: 76% (S)

(S)-1-(2,6-dichloro-3-fluorophenyl)ethanol

The product was purified by column chromatography using 100% hexane followed by dichloromethane/methanol (95/5) to give the product as a colourless oil. 300 mg 2',6'-dichloro-3'-fluoroacetophenone (1.45 mmol) gave 242 mg product (1.16 mmol) (80%).

$^1$H-NMR (CDCl$_3$) δ: 7.29 (1H, m, Ar—H), 7.05 (1H, t, J=7.9 Hz, Ar—H), 5.60 (1H, q, J=6.4 Hz, Ar—CH(OH)—CH$_3$), 1.67 (3H, d, J=6.4 Hz, Ar—CH(OH)—CH$_3$);

$^{13}$C-{$^1$H}-NMR (DEPT, CDCl$_3$) δ: 158.27 (Ar—C), 156.29 (Ar—C), 140.51 (Ar—C), 129.16 ((CH(OH)—C$_{Ar}$), 115.78 (Ar—C), 115.60 (Ar—C), 68.44 (—CH(OH)—), 21.38 (—CH$_3$);

HRMS (EI+): calculated for [C$_8$H$_7$Cl$_2$FO]: 207.9858 (100%)/209.9828; found: 207.9868/209.9845.

Chiral analysis was performed using a Chiralpak OD-H column using n-hexane/isopropanol (98/2) mobile phase at a flowrate of 0.5 mL/min. t$_R$ (S, major): 17.4 min; t$_R$(R, minor): 18.2 min, ee=82 (S) %

(S)-1-(4-chlorophenyl)-1-propanol

The product was purified by column chromatography using 100% hexane followed by hexanes/ethyl acetate (1/1) to give the product as a colourless oil. 275 mg 4'-chloropropiophenone (1.30 mmol, 1 equiv.) gave 220 mg product (1.34 mmol, 79%).

$^1$H-NMR (CDCl$_3$) δ: 7.36-7.28 (4H, m, C$_{Ar}$H), 4.61 (1H, t, J=6.9 Hz, Ar—CH(OH)CH$_2$CH$_3$), 1.78 (2H, m, Ar—CH(OH)CH$_2$CH$_3$), 0.98 (3H, t, J=7.8 Hz, —CH$_3$);

$^{13}$C-{$^1$H}-NMR (DEPT, CDCl$_3$) δ: 143.00 (Cl—C$_{Ar}$), 133.09 (C$_{Ar}$), 128.52 (C$_{Ar}$), 127.36 (C$_{Ar}$), 75.10 (—CH(OH)—), 31.97 (—CH$_2$—), 10.00 (—CH$_3$);

Chiral analysis was performed using a Chiralpak OD-H column using n-hexane/isopropanol (99/1) mobile phase at a flowrate of 1.0 mL/min. ee=80% (S)

1-(4-methoxyphenyl)-1-propanol

The product was purified by column chromatography using first hexane and then methylene chloride/methanol (95/5) as the mobile phase to give the product as an oil. NMR analysis showed that the conversion was 96% to product. Using 262 mg (1.70 mmol) of 4'-methoxypropiophenone, 190 mg (1.21 mmol) of product was isolated (71% yield);

$^1$H-NMR (CDCl$_3$) δ: 7.29 (2H, d, J=8.6 Hz, C$_{Ar}$H), 6.91 (2H, d, J=8.6 Hz, C$_{Ar}$H), 4.57 (1H, t, J=6.7 Hz, Ar—CH(OH)—CH$_3$), 3.83 (3H, s, —OCH$_3$), 1.95-1.39 (2H, m, —CH$_2$—), 0.92 (3H, t, J=7.4 Hz, Ar—CH(OH)CH$_2$CH$_3$);

$^{13}$C-{$^1$H}-NMR (DEPT, CDCl$_3$) δ: 159.00 (MeO—$\underline{C}_{Ar}$), 136.75 ((CH(OH)—$\underline{C}_{Ar}$), 127.22 ($\underline{C}_{Ar}$), 113.78 ($\underline{C}_{Ar}$), 75.69 (—OCH$_3$) 55.30 (—$\underline{C}$H(OH)—), 31.79 (—$\underline{C}$H$_2$—), 10.25 (—$\underline{C}$H$_3$);

HRMS (EI+): calculated for [C$_{10}$H$_{14}$O$_2$]: 166.0990 (100%); found: 166.0994 (100%).

Chiral analysis was performed using a Chiralpak OD-H column using $^n$hexane/isopropanol (96/4) mobile phase at a flowrate of 1.0 mL/min. ee=70% (S)

2-methyl-1-phenyl-1-propanol

The product was purified by column chromatography using first hexanes and then methylene chloride/methanol (95/5) to give the product as a pale-yellow oil. Using 250 mg (1.69 mmol) of isobutyrophenone, 228 mg (1.52 mmol) of title compound was isolated (90% yield);

$^1$H-NMR (CDCl$_3$) δ: 7.38-7.28 (5H, m, Ph-H), 4.38 (1H, d, J=7.6 Hz, Ph-C$\underline{H}$(OH)—), 2.24 (2H, m, —C$\underline{H}$—(CH$_3$)$_2$ and —O$\underline{H}$), 1.92 (1H, m, —CH—(C$\underline{H}_2$)$_4$—), 1.03 (3H, d, J=6.7 Hz, —CH—(C$\underline{H}_3$)$_2$), 0.82 (3H, d, J=6.7 Hz, —CH—(C$\underline{H}_3$)$_2$);

$^{13}$C-{$^1$H}-NMR (CDCl$_3$) δ: 143.65 (($\underline{C}_{Ar}$—CH(OH)), 128.19 (Ar—C), 127.42 (Ar—C), 126.59 (Ar—C), 80.05 (—$\underline{C}$H(OH)—), 35.27 (—$\underline{C}$H(CH$_3$)$_2$), 19.02 (—CH($\underline{C}$H$_3$)$_2$), 18.29 (—CH($\underline{C}$H$_3$)$_2$);

HRMS (EI+): calculated for [C$_{10}$H$_{14}$O]: 150.105 found: 150.104.

Chiral analysis was performed using a Chiralcel OD-H column using $^n$hexane/isopropanol (98/2) mobile phase, flow 0.5 mL/min, t$_R$ (S, minor): 25.0 min; t$_R$ (R, major): 29.8 min, ee: 90% (S)

Synthesis of (R$_c$,S$_p$)-1-(2-bis(4-methoxy-3,5-dimethylphenyl)phosphine)-ferrocenylethylamine L-tartrate salt (3)

(R$_c$,S$_p$)-3 (shown without tartrate salt) (R$_c$,S$_p$)—N,N-dimethyl-1-(2-bis(4-methoxy-3,5-dimethylphenyl)phosphine)-ferrocenylethylamine (6.3 g, 11.3 mmol) was stirred in degassed acetic anhydride (30 mL) at room temperature or 16 h. The volatiles were removed by evaporation and the crude acetate dissolved in a degassed mixture of methanol (60 mL) and THF (60 mL). Aqueous ammonium hydroxide (30 wt %, 60 mL) was added and the mixture heated to 60° C. for 2 h, then cooled to room temperature and all the volatiles removed in vacuo. The crude mixture was treated with degassed saturated aqueous sodium bicarbonate (60 mL) and extracted with degassed dichloromethane (3×60 mL). The organic extracts were cannulated to a Schlenck flask containing magnesium sulfate under an argon atmosphere. The combined extracts were filtered using a cannula fitted with a filter paper into a flask and the solvent removed. The crude material was dissolved in degassed ethanol (60 mL) and L-tartaric acid (1.44 g, 9.6 mmol, 0.85 equiv.) added. The mixture was heated to reflux under an argon atmosphere and distilled to half-volume, cooled to room temperature and the product salt precipitated by the addition of diethyl ether (200 mL). Isolation by filtration and washing with diethyl ether gave the title compound as a yellow solid (6.0 g, 8.8 mmol, 78% yield).

$^1$H-NMR (MeOD) δ: 7.29 (1H, s, C$_{Ar}$H), 7.27 (1H, S, C$_{Ar}$H), 6.87 (1H, S, C$_{Ar}$H), 6.86 (1H, s, C$_{Ar}$H), 4.97 (7H, br s, H$_2$O, —OH, —NH$_2$, CO$_2$H), 4.69 (1H, s, Fc-H), 4.56 (2H, br s, —C$\underline{H}$— and Fc-H), 4.43 (2H, m, HO$_2$C(C$\underline{H}$)$_2$CO$_2$H), 4.12 (1H, m, Fc-H), 4.05 (5H, s, Fc-H), 3.77 (3H, s, —OCH$_3$), 3.71 (3H, s, —OCH$_3$), 2.32 (6H, s, —CH$_3$), 2.20 (6H, s, —CH$_3$), 1.79 (3H, br d, J=8.1 Hz, CHCH$_3$);

$^{13}$C{$^1$H}-NMR (CDCl$_3$) δ: 158.33 (s, C$_{Ar}$), 157.40 (S, C$_{Ar}$), 135.41 (S, C$_{Ar}$), 135.23 (S, C$_{Ar}$), 134.06 (d, J$_{PC}$=5.9 Hz, C$_{Ar}$), 132.68 (S, C$_{Ar}$), 132.53 (S, C$_{Ar}$), 131.46 (d, J$_{PC}$=5.8 Hz, C$_{Ar}$), 131.02 (d, J$_{PC}$=7.3 Hz, C$_{Ar}$), 130.07 (d, J$_{PC}$=9.7 Hz, C$_{Ar}$), 91.02 (d, J$_{PC}$=26.8 Hz, Fc-C$^{ipso}$—P), 76.3 (d, J$_{PC}$=11.3 Hz, C$_{Fc}$), 72.80 (C$_{Fc}$), 72.37 (HO$_2$C($\underline{C}$HOH)$_2$CO$_2$H), 70.05 (C$_{Fc}$), 69.77 (C$_{Fc}$), 69.19 (C$_{Fc}$), 58.83 (—OCH$_3$), 57.83 (—OCH$_3$), 46.30 (d, J$_{PC}$=9.7 Hz, Fc-$\underline{C}$H(CH$_3$)—N), 19.15 (Fc-CH($\underline{C}$H$_3$)—N), 14.88 (Ar—$\underline{C}$H$_3$);

$^{31}$P{$^1$H}-NMR (CDCl$_3$) δ: –28.7 (s);

IR (ATR, cm$^{-1}$): 2927.9 (m), 2358.9 (w), 2160.3 (m), 2019.5 (w), 1473.6 (m), 1273.0 (m), 1217.1 (s), 1109.1 (s), 1072.4 (s), 1010.7 (s), 817.8 (m), 678.9 (m), 607.6 (m);

HRMS: (ES+) calculated for [C$_{30}$H$_{37}$FeNO$_2$P]$^+$ 530.1906; found 530.1890;

Synthesis of 4-(dimethylamino)pyridine-2-carboxaldehyde (4)

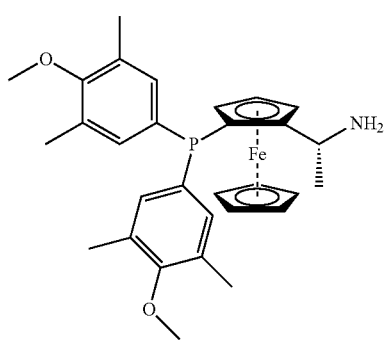

(R$_c$, S$_p$)-3

(shown without tartrate salt)

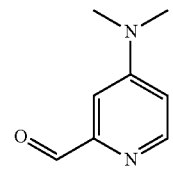

4

2-dimethylaminoethanol (1.7 mL, 17.0 mmol, 2.1 equiv.) was dissolved in $^n$hexane (20 mL) and cooled to –10° C. under an inert atmosphere. N-Butyl lithium (1.6 M, 20 mL, 32 mmol, 3.9 equiv.) was slowly added to the cold solution. The resulting clear colourless solution was stirred at –10° C. for 30 min then 4-dimethylaminopyridine (1.0 g, 8.2 mmol, 1.0 equiv.) was added as a solid. The yellow slurry was stirred at −10° C. for 2 h then cooled to −78° C. and dimethylformamide (1 mL, 12.9 mmol, 1.6 equiv.) in THF (15 mL) was added. 1 M aqueous hydrochloric acid (50 mL) was added after 1 h and the mixture allowed to warm to room temperature and the layers separated. The aqueous layer was found to have a pH of 1 and was extracted with diethyl ether (3×50 mL). The organic extractions were discarded. The pH was adjusted to 7 using solid sodium bicarbonate and the mixture again extracted with diethyl ether (3×50 mL). The combined organic layers were dried over magnesium sulfate, filtered and concentrated to dryness to give the title compound as a pale brown oil (0.65 g, 4.3 mmol, 53%).

$^{1}$H-NMR (CDCl$_3$) δ: 10.01 (1H, s, —CHO), 8.40 (1H, d, J=6.0 Hz, C$_{Ar}$H), 7.20 (1H, d, J=2.8 Hz, C$_{Ar}$H), 6.68 (1H, dd, J=6.0/2.8 Hz, C$_{Ar}$H), 6.10 (1H, d, J=2.1 Hz, C$_{Ar}$H), 3.09 (6H, s, —N(CH$_3$)$_2$);

$^{13}$C-{$^{1}$H}-NMR (CDCl$_3$) δ: 194.59 (—CHO), 154.70 (C$_{Ar}$), 152.95 (C$_{Ar}$), 150.05 (C$_{Ar}$), 109.87 (C$_{Ar}$), 104.37 (C$_{Ar}$), 39.24 (—N(CH$_3$)$_2$).

Synthesis of (R$_c$, S$_p$)—N-[4-(dimethylamino)pyridine-2-methyl]-1-(2-bis(4-methoxy-3, 5-dimethylphenyl)phosphine)ferrocenylethylamine L-tartrate salt (5)

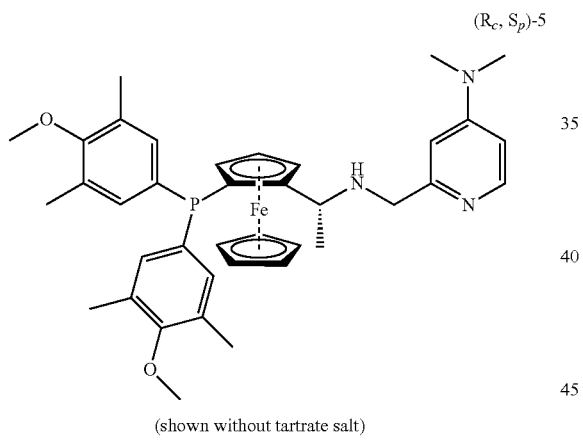

(R$_c$, S$_p$)-5

(shown without tartrate salt)

(R$_c$, S$_p$)-1-(2-bis(4-methoxy-3,5-dimethylphenyl)phosphine)ferrocenylethylamine (2.1 g, 4.0 mmol, 1.0 equiv.) was treated with 4-(dimethylamino)pyridine-2-carboxaldehyde (0.60 g, 4.0 mmol, 1.0 equiv.) and stirred at room temperature in degassed dry methanol (20 mL) for 2 h. Sodium borohydride (303 mg, 8.0 mmol, 2.0 equiv.) was added and the resulting mixture stirred for another 2 h at room temperature under an inert atmosphere. Volatiles were removed in vacuo and the crude material added to saturated aqueous sodium bicarbonate (20 mL) and extracted with dichloromethane (3×20 mL). The extracts were cannulated to a Schlenk flask containing magnesium sulfate. The dried combined organic extracts were filtered using a cannula fitted with a filter paper and concentrated to give (R$_c$, S$_p$)—N-[4-(dimethylamino)pyridine-2-methyl]-1-(2-bis(4-methoxy-3,5-dimethylphenyl)phosphine)-ferrocenylethylamine as an orange foam (2.6 g, 3.92 mmol, 98%). 200 mg (0.30 mmol, 1.0 equiv.) was treated with 45 mg (0.30 mmol, 1.0 equiv) of L-tartaric acid in isopropanol (5 mL) as per the previous description (see synthesis of compound 3) to give the title compound as a yellow solid (147 mg, 0.18 mmol, 60%).

$^{1}$H-NMR (MeOD) δ: 7.81 (1H, br s, Py-H), 7.25 (1H, s, C$_{Ar}$H), 7.23 (1H, S, C$_{Ar}$H), 6.91 (1H, S, C$_{Ar}$H), 6.90 (1H, S, C$_{Ar}$H), 6.77 (1H, br s, Py-H), 6.36 (1H, br s, Py-H), 4.94 (12H, br s, H$_2$O, —OH, —NH$_2$, CO$_2$H), 4.64 (1H, s, Fc-H), 4.48 (3H, br s, HO$_2$C(CH)$_2$CO$_2$H and Fc-H), 4.43 (1H, br s, —CH(CH$_3$)—), 4.04 (5H, s, Fc-H), 4.02 (1H, s, Fc-H), 3.76 (3H, —OCH$_3$), 3.61 (3H, s, —OCH$_3$), 3.53 (2H, m, —CH$_2$Py), 3.13 (6H, s, —N(CH$_3$)$_2$), 2.30 (6H, s, —CH$_3$), 2.09 (6H, s, —CH$_3$), 1.79 (3H, br d, J=7.5 Hz, CHCH$_3$);

$^{13}$C{$^{1}$H}—NMR (MeOD) δ: 158.09 (S, C$_{Ar}$), 157.24 (s, C$_{Ar}$), 151.59 (s, C$_{Ar}$), 139.09 (S, C$_{Ar}$), 135.25 (s, C$_{Ar}$), 135.08 (S, C$_{Ar}$), 134.75 (d, J$_{PC}$=8.6 Hz, C$_{Ar}$), 133.0 (s, C$_{Ar}$), 132.84 (s, C$_{Ar}$), 131.30 (d, J$_{PC}$=6.6 Hz, C$_{Ar}$), 130.81 (d, J$_{PC}$=6.6 Hz, C$_{Ar}$), 130.49 (d, J$_{PC}$=8.6 Hz, C$_{Ar}$), 105.83 (C$_{Ar}$), 103.75 (S, C$_{Ar}$), 94.64 (d, J$_{PC}$=26.4 Hz, Fc-C$^{ipso}$—P), 76.06 (d, J$_{PC}$=8.2 Hz, C$_{Fc}$), 72.72 (HO$_2$C(CHOH)$_2$CO$_2$H), 71.57 (C$_{Fc}$), 69.53 (C$_{Fc}$), 69.24 (C$_{Fc}$), 69.19 (C$_{Fc}$), 58.83 (—OCH$_3$), 57.83 (—OCH$_3$), 51.74 (d, J$_{PC}$=10.4 Hz, Fc-CH(CH$_3$)—N), 45.79 (s, —CH$_2$Py), 38.67 (s, —N(CH$_3$)$_2$), 17.70 (Fc-CH(CH$_3$)—N), 14.78 (Ar—CH$_3$);

$^{31}$P-{$^{1}$H}—NMR (CDCl3) δ: −28.4 (s);

IR (ATR): 2922.2 (w), 2358.9 (w), 1639.5 (m), 1556.6 (m), 1473.6 (w), 1273.0 (w), 1217.1 (s), 1111.0 (s), 1006.8 (s), 817.8 (m), 609.5 (m) cm$^{-1}$;

HRMS: (ES+) calculated for [C$_{38}$H$_{47}$FeN$_3$O$_2$P]$^{+}$ 664.2750; found 664.2733

Synthesis of [(R$_c$,S$_p$)—N-(4-(dimethylamino)pyridine-2-methyl)-1-(~2-bis(4-methoxy-3,5-dimethylphenyl)phosphino)ferrocenylethylamine]-κN$^{1}$-κN$^{2}$-κ$^{P}$-tricarbonyl manganese (I) bromide (6)

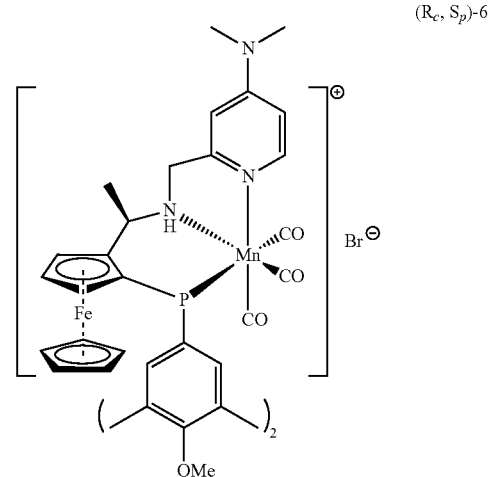

(R$_c$, S$_p$)-6

(R$_c$,S$_p$)—N-(4-dimethylaminopyridine-2-methyl)-1-(2-bis(4-methoxy-3,5-dimethyl-phenyl)phosphine)ferrocenylethylamine (2.4 g, 3.62 mmol, 1.02 equiv.) and bromopentacarbonylmanganese (I) (975 mg, 3.55 mmol, 1.0 equiv.) were stirred in degassed cyclohexane (50 mL) at room temperature under an argon atmosphere. The mixture was refluxed for 16 h under which time an orange slurry formed. The mixture was cooled to room temperature, diluted with ″hexane (40 mL), filtered, and washed with ″hexane (20 mL). The crude material was dissolved in dichloromethane (10 mL) and filtered. ⁿhexane (30 mL) was added and the resulting mixture slowly evaporated until product precipitated. The product was filtered, washed with ⁿhexane and dried to give the title compound as a yellow solid (2.87 g, 3.27 mmol, 92%). Analysis showed two species that could not be separated.

$^1$H-NMR (DCM-d$_2$) δ (major): 8.04 (1H, br d, J=7.5 Hz, C$_{Ar}$H), 7.65 (1H, s, C$_{Ar}$H), 7.63 (1H, s, C$_{Ar}$H), 6.33 (1H, C$_{Ar}$H overlap with minor), 6.01 (2H, s, C$_4$r, overlap with minor), 5.58 (1H, d, J=6.9 Hz, —CH—, overlaps with minor), 4.84 (1H, s, NH), 4.60 (1H, s, Fc-H), 4.45 (1H, s, Fc-H), 4.33 (1H, s, Fc-H), 3.95 (1H, m, PyCH$_2$NH—, overlap with minor), 3.84 (5H, s, Fc-H, overlap with minor), 3.80 (3H, s, —OCH$_3$, overlap with minor), 3.58 (1H, m, PyCH$_2$NH, overlap with minor), 3.52 (3H, s, —OCH$_3$), 2.86 (6H, s, —N(CH$_3$)$_2$, overlap with minor) 2.39 (6H, s, —CH$_3$), 1.98 (6H, s, —CH$_3$, overlap with minor), 1.68 (3H, br d, J=6.9 Hz, CHC$\underline{H}_3$, overlap with minor); b(minor): 7.69 (1H, s, C$_{Ar}$H), 7.67 (1H, s, C$_{Ar}$H), 7.37 (1H, br d, J=6.2 Hz, C$_{Ar}$H) 6.33 (1H, CArH overlap with major), 6.01 (2H, s, C$_4$r, overlap with major), 5.95 (1H, s, C$_{Ar}$H), 5.58 (1H, d, J=6.9 Hz, —CH—, overlap with major), 4.93 (1H, s, NH), 4.69 (1H, s, Fc-H), 4.57 (1H, s, Fc-H), 3.95 (1H, m, PyCH$_2$NH—, overlap with major), 3.84 (5H, s, Fc-H, overlap with major), 3.80 (3H, s, —OCH$_3$, overlap with major), 3.58 (4H, m, PyCH$_2$NH and —OCH$_3$, overlap with major), 2.86 (6H, s, —N(CH$_3$)$_2$, Overlap with major) 2.43 (6H, s, —CH$_3$), 1.98 (6H, s, —CH$_3$, overlap with major), 1.68 (3H, br d, J=6.9 Hz, CHC$\underline{H}_3$, overlap with major);

$^{13}$C{$^1$H}—NMR (DCM-d$_2$) b(major): 231.84 (d, J$_{PC}$=22 Hz, CO), 230.02 (d, J$_{PC}$=23.5 Hz, CO), 158.37 (C$_{Ar}$), 153.95 (C$_{Ar}$), 151.64 (C$_{Ar}$), 150.48 (C$_{Ar}$), 140.70 (d, J$_{PC}$=34 Hz, C$_{Ar}$), 136.85 (C$_{Ar}$), 136.43 (O$_{Ar}$), 134.25 (d, J$_{PC}$=10.0 Hz, C$_{Ar}$), 130.61 (d, J$_{PC}$=8.6 Hz, C$_{Ar}$), 130.27 (C$_{Ar}$), 127.80 (C$_{Ar}$), 127.48 (d, J$_{PC}$=10.1 Hz, C$_{Ar}$), 106.90 (O$_{Ar}$), 101.93 (C$_{Ar}$), 91.87 (d, J$_{PC}$=18.6 Hz, Fc-C$^{ipso}$—P), 72.70 (C$_{Fc}$), 70.66 (C$_{Fc}$), 56.69 (Py-1H$_2$—N), 48.73 (Fc-C$\underline{H}$(CH$_3$)—N), 39.22 (—N(CH$_3$)$_2$), 20.58 (Fc-CH(C$\underline{H}_3$)—N); δ (minor): 159.82 (C$_{Ar}$), 154.31 (C$_{Ar}$), 150.48 (C$_{Ar}$), 134.51 (d, J$_{PC}$=10.6 Hz, C$_{Ar}$), 131.47 (C$_{Ar}$), 131.16 (C$_{Ar}$), 128.83 (C$_{Ar}$), 128.10 (d, J$_{PC}$=8.6 Hz, C$_{Ar}$), 127.68 (O$_{Ar}$), 107.84 (O$_{Ar}$), 102.96 (O$_{Ar}$), 92.51 (d, J$_{PC}$=23.1 Hz, Fc-C$^{ipso}$—P), 73.21 (C$_{Fc}$), 71.42 (C$_{Fc}$), 70.94 (C$_{Fc}$), 70.07 (C$_{Fc}$), 58.04 (Py-CH$_2$—N), 49.79 (Fc-C$\underline{H}$(CH$_3$)—N), 39.37 (—N(CH$_3$)$_2$), 19.64 (Fc-CH(C$\underline{H}_3$)—N);

$^{31}$P-{$^1$H}—NMR (DCM-d$_2$) δ: +89.1 (s, major), 43.6 (br s, minor);

IR (ATR): 2953.0 (w), 2918.3 (w), 2895.2 (w), 2025.3 (s), 1942.3 (m), 1909.5 (s), 1830.5 (s), 1616.4 (s), 1473.6 (m), 1276.9 (m), 1219.0 (m), 1111.0 (s), 1008.8 (s), 839.0 (s), 617.2 (s) cm$^{-1}$;

HRMS: (ESI positive): expected [C$_{41}$H$_{46}$FeMnN$_3$O$_5$P]$^+$: 802.1900, found: 802.1889.

Use of 6 in Ketone Hydrogenation

General Ketone Hydrogenation Procedure

Ketone (1.0 equiv.), manganese catalyst (0.001 equiv.), potassium carbonate (0.05 equiv.) and 1-methylnaphthalene (~50 µL, internal standard) was added to a microwave vial containing a stirring bead. The vial was sealed and evacuated and refilled with argon. This was repeated twice. Degassed ethanol (3.0 mL) was added and the vial septum as pierced with 2×18G needles and placed in a stainless-steel autoclave under argon atmosphere. The vessel was pressurised with hydrogen gas (50 bar) and vented to the atmosphere. This was repeated twice. The pressure was set to 50 bar using hydrogen gas and the autoclave sealed and placed in a pre-heated oil bath (50° C.) and the stirring as set to 1200 rpm and left for 16 h. After the reaction, the vessel was cooled to ambient temperature and vented to the atmosphere, the reaction was analysed by $^1$H-NMR and conversion was estimated using the internal standard (1-methylnaphthalene). The reaction mixture was evaporated to dryness and the crude product was purified by column chromatography as detailed below.

For activity comparison experiments: the setup was the same as above but the reaction time was shortened to 2 h.

EXAMPLES (S)-1-phenylethanol

The product was purified by column chromatography using 100% hexane followed by hexanes/ethyl acetate (1/1) to give the product as a colourless oil. 250 mg acetophenone (2.1 mmol) gave 250 mg product (98%).

$^1$H-NMR (CDCl$_3$) δ: 7.39 (4H, m, Ar—H), 7.31 (1H, m, Ar—H), 4.93 (1H, q, J=6.2 Hz, Ar—C$\underline{H}$(OH)—CH$_3$), 1.53 (3H, d, J=6.2 Hz, Ar—CH(OH)—C$\underline{H}_3$);

$^{13}$C-{$^1$H}—NMR (DEPT, CDCl$_3$) δ: 145.80 (C$_{Ar}$—CH (OH)—), 128.52 (Ar—C), 127.50 (Ar—C), 125.39 (Ar—C), 70.46 (—C$\underline{H}$(OH)—), 25.20 (—C$\underline{H}_3$);

HRMS (EI+): calculated for [C$_8$H$_{10}$O]: 122.0732; found: 122.0734.

Chiral analysis was performed using a Chiralcel OD-H column using n-hexane/isopropanol (90/10) mobile phase at a flowrate of 0.5 mL/min. t$_R$ (S, minor): 12 min; t$_R$(R, major): 14 min, e.e. 68%

(S)-1-(2-fluorophenyl)ethanol

The product was purified by column chromatography using 100% hexane followed by hexanes/ethyl acetate (1/1) to give the product as a colourless oil. 265 mg 2'-Fluoroacetophenone (1.9 mmol) gave 200 mg product (74%).

$^1$H-NMR (CDCl$_3$) δ: 7.51 (1H, td, J=7.9/1.7 Hz C$_{Ar}$H), 7.27 (1H, m, C$_{Ar}$H), 7.18 (1H, td, J=7.5/1.3 Hz, C$_{Ar}$H), 7.04 (1H, m, C$_{Ar}$H), 5.23 (1H, m, Ph-C$\underline{H}$(OH)—CH$_3$), 2.03 (1H, d, J=4.5 Hz, —OH), 1.54 (3H, d, J=6.4 Hz, Ar—CH(OH)—C$\underline{H}_3$);

$^{13}$C-{$^1$H}—NMR (DEPT, CDCl$_3$) δ: 160.9 (C$_{Ar}$), 158.51 (C$_{Ar}$), 128.82 (C$_{Ar}$), 128.74 (C$_{Ar}$), 126.65 (C$_{Ar}$), 124.30 (C$_{Ar}$), 115.10 (C$_{Ar}$), 64.60 (—C$\underline{H}$(OH)—), 24.02 (—C$\underline{H}_3$)

Chiral analysis was performed using a Chiralcel OD-H column using n-hexane/isopropanol (98/2) mobile phase at a flowrate of 0.5 mL/min; e.e. 56%

(S)-1-(2-chlorophenyl)ethanol

The product was purified by column chromatography using 100% hexane followed by hexanes/ethyl acetate (1/1) to give the product as a colourless oil. 262 mg 2'-chloroacetophenone (1.7 mmol) gave 238 mg product (90%).

$^1$H-NMR (CDCl$_3$) δ: 7.61 (1H, d, J=7.5 Hz, Ar—H), 7.33 (2H, m, Ar—H), 7.22 (1H, t, J=8.6 Hz, Ar—H), 5.31 (1H, q, J=6.6 Hz, Ar—C$\underline{H}$(OH)—CH$_3$), 1.51 (3H, d, J=6.4 Hz, Ar—CH(OH)—C$\underline{H}_3$);

$^{13}$C-{$^1$H}—NMR (DEPT, CDCl$_3$) δ: 143.05 (Cl—C$_{Ar}$), 131.63 ((CH(OH)—C$_{Ar}$), 129.04 (Ar—C), 128.41 (Ar—C), 127.22 (Ar—C), 126.41 (Ar—C), 66.97 (—C$\underline{H}$(OH)—), 23.52 (—C$\underline{H}_3$);

HRMS (EI+): calculated for [C8H9ClO]: 156.0342 (100%)/158.0312 (32%); found: 156.0345 (100%)/158.0313 (32%).

Chiral analysis was performed using a Chiralcel OD-H column using n-hexane/isopropanol (95/5) mobile phase at a flowrate of 0.5 mL/min. $t_R$ (S, minor): 13 min; $t_R$ (R, major): 15 min, e.e. 56%

(S)-1-(2-methoxyphenyl)ethanol

The product was purified by column chromatography using 100% hexane followed by hexanes/ethyl acetate (1/1) to give the product as a colourless oil. 289 mg 2'-methoxyacetophenone (1.9 mmol) gave 265 mg product (90%).

$^1$H-NMR (CDCl$_3$) δ: 7.37 (1H, d, J=6.8 Hz, Ar—H), 7.28 (1H, m, Ar—H), 6.99 (1H, t, J=8.1 Hz, Ar—H), 6.91 (1H, d, J=7.9 Hz, Ar—H), 5.12 (1H, q, J=6.5 Hz, Ar—CH(OH)—CH$_3$), 3.89 (3H, s, —OCH$_3$), 1.54 (3H, d, J=6.5 Hz, Ar—CH(OH)—CH$_3$);

$^{13}$C-{$^1$H}—NMR (DEPT, CDCl$_3$) δ: 156.57 (MeO—C$_{Ar}$), 133.37 ((CH(OH)—C$_{Ar}$), 128.32 (Ar—C), 126.12 (Ar—C), 120.80 (Ar—C), 110.42 (Ar—C), 66.62 (—OCH$_3$) 55.27 (—CH(OH)—), 22.83 (—CH$_3$);

HRMS (EI+): calculated for [C$_9$H$_{12}$O$_2$]: 152.0837 (100%); found: 152.0836 (100%).

Chiral analysis was performed using a Chiralpak OD-H column using n-hexane/isopropanol (98/2) mobile phase at a flowrate of 1.0 mL/min. $t_R$ (S, major): 19.3 min; $t_R$(R, minor): 20.4 min, e.e. 56%

(S)-1-(2,6-dichloro-3-fluorophenyl)ethanol

The product was purified by column chromatography using 100% hexane followed by dichloromethane/methanol (95/5) to give the product as a colourless oil. 345 mg 2',6'-dichloro-3'-fluoroacetophenone (1.66 mmol) gave 278 mg product (80%).

$^1$H-NMR (CDCl$_3$) δ: 7.29 (1H, m, Ar—H), 7.05 (1H, t, J=7.9 Hz, Ar—H), 5.60 (1H, q, J=6.4 Hz, Ar—CH(OH)—CH$_3$), 1.67 (3H, d, J=6.4 Hz, Ar—CH(OH)—CH$_3$);

$^{13}$C-{$^1$H}—NMR (DEPT, CDCl$_3$) δ: 158.27 (Ar—C), 156.29 (Ar—C), 140.51 (Ar—C), 129.16 ((CH(OH)—C$_{Ar}$), 115.78 (Ar—C), 115.60 (Ar—C), 68.44 (—CH(OH)—), 21.38 (—CH$_3$);

HRMS (EI+): calculated for [C$_8$H$_7$Cl$_2$FO]: 207.9858 (100%)/209.9828; found: 207.9868/209.9845.

Chiral analysis was performed using a Chiralpak OD-H column using n-hexane/isopropanol (98/2) mobile phase at a flowrate of 0.5 mL/min. $t_R$ (S, major): 17.4 min; $t_R$(R, minor): 18.2 min, e.e. 82%

(S)-1-(4-chlorophenyl)-1-propanol

The product was purified by column chromatography using 100% hexane followed by hexanes/ethyl acetate (1/1) to give the product as a colourless oil. 229 mg 4'-chloropropiophenone (1.36 mmol, 1 equiv.) gave 200 mg product (86%).

$^1$H-NMR (CDCl$_3$) b: 7.36-7.28 (4H, m, C$_{Ar}$H), 4.61 (1H, t, J=6.9 Hz, Ar—CH(OH)CH$_2$CH$_3$), 1.78 (2H, m, Ar—CH(OH)CH$_2$CH$_3$), 0.98 (3H, t, J=7.8 Hz, —CH$_3$);

$^{13}$C-{$^1$H}—NMR (DEPT, CDCl$_3$) δ: 143.00 (Cl—C$_{Ar}$), 133.09 (C$_{Ar}$), 128.52 (C$_{Ar}$), 127.36 (C$_{Ar}$), 75.10 (—CH(OH)—), 31.97 (—CH$_2$—), 10.00 (—CH$_3$);

Chiral analysis was performed using a Chiralpak OD-H column using n-hexane/isopropanol (99/1) mobile phase at a flowrate of 1.0 mL/min. e.e. 86% (S)

(S)-1-phenyl-1-cyclohexylmethanol

The product was purified by column chromatography using 100% hexane followed by hexanes/ethyl acetate (1/1) to give the product as a white solid. 255 mg Cyclohexylphenylketone (1.36 mmol) gave 230 mg product (89%).

$^1$H-NMR (CDCl$_3$) δ: 7.40-7.27 (5H, m, Ph-H), 4.39 (1H, dd, J=7.2/2.9 Hz, Ph-CH(OH)—C$_6$H$_{11}$), 2.02 (1H, m, —CH$_2$—), 1.87 (1H, m, —CH—), 1.80 (1H, m, —CH$_2$—), 1.66 (3H, m, —CH$_2$—), 1.40 (1H, m, —CH$_2$—), 1.32-0.91 (5H, m, —CH$_2$—);

$^{13}$C-{$^1$H}—NMR (DEPT, CDCl$_3$) δ: 143.62 ((C$_{Ar}$—CH(OH)), 128.20 (C$_{Ar}$), 127.43 (C$_{Ar}$), 126.65 (C$_{Ar}$), 79.42 (—CH(OH)—), 44.97 (—CH(CH$_2$)$_5$), 29.32 (—CH$_2$—), 28.85 (—CH$_2$—), 26.44 (—CH$_2$—), 26.11 (—CH$_2$—), 26.03 (—CH$_2$—);

Chiral analysis was performed using a Chiralcel OD-H column using ″hexane/isopropanol (98/2) mobile phase, flow 1.0 mL/min, $t_R$ (S, major): 12.2 min; $t_R$ (R, minor): 14.2 min, e.e. 82%

Kinetic Study of Ketone Hydrogenation Using Hydrogen Gas-Uptake Measuring Apparatus.

Acetophenone (2.5 g, 20.81 mmol, 1.0 equiv.) was dissolved in ethanol (30 mL) and degassed by bubbling argon gas through the solution for 1 h. Catalyst (0.011-0.021 mmol, 0.0005-0.001 equiv.) and potassium carbonate (144 mg, 1.04 mmol, 0.05 equiv.) was charged to an autoclave. The vessel was sealed and pressurised with hydrogen gas (5 bar) and vented. This was repeated twice. The degassed ethanol solution was added via an injection port and the vessel sealed and pressurised with hydrogen gas (20 bar) and vented. This was repeated twice. The pressure was set to 2 bar and the mixture heated to 50° C. at which time the pressure was increased to 20 bar and the experiment started. Gas uptake was monitored by reduction of the pressure in the burette. The reaction was considered complete after no gas uptake was observed for >2 h. The vessel was cooled to room temperature, vented and the content concentrated to dryness and analysed by $^1$H-NMR to confirm full conversion. The uptake curve was converted to conversion by dividing the gas uptake at a time-point by total uptake and multiplied by 100 to get percentage conversion. Substrate and product concentrations could be calculated, from which the turnover frequency (TOF) could be calculated. The TOF was reported at 20% conversion to minimise temperature influence of the vessel setup.

TABLE 1

Hydrogenation of various ketones using 6

| Substrate | Catalyst loading | Reaction Temp. (° C.) | Reaction time (h) | Conversion | e.e.[b] |
|---|---|---|---|---|---|
| Acetophenone | 0.1 mol % | 50 | 16 h | >99% | 68% (S) |
| Acetophenone | 0.02 mol % | 60 | 16 h | >99% | 51% (S) |
| Acetophenone | 0.01 mol % | 65 | 24 h | >99% | 57% (S) |
| 2'-Fluoroacetophenone | 0.1 mol % | 50 | 16 h | >99% | 56% (S) |
| 2'-Chloroacetophenone | 0.1 mol % | 50 | 16 h | >99% | 56% (S) |

TABLE 1-continued

Hydrogenation of various ketones using 6

| Substrate | Catalyst loading | Reaction Temp. (° C.) | Reaction time (h) | Conversion | e.e.[b] |
|---|---|---|---|---|---|
| 2'-methoxyacetophenone | 0.1 mol % | 50 | 16 h | >99% | 60% (S) |
| 2',6'-dichloro-3-fluoroacetophenone | 0.1 mol % | 50 | 16 h | >99% | 82% (S) |
| 4'-Chloropropiophenone | 0.1 mol % | 50 | 16 h | >99% | 80% (S) |
| Cyclohexylphenylketone | 0.1 mol % | 50 | 16 h | >99% | 82% (S) |

Typical conditions: 1.9 mmol substrate, 0.0019 mmol catalyst, 0.10 mmol $K_2CO_3$, 50 bar hydrogen gas, ethanol (2.7 mL), 16 h;
[b]determined using chiral HPLC; absolute configuration in brackets.

The data in Table 1 indicates that 6 is effective at catalysing the hydrogenation of various ketones at low catalyst loadings (about 0.01 to about 0.1 mol %) and at low temperatures (about 50 to about 60° C.). All of the ketones exemplified in Table 1 are pro-chiral, and form optically active alcohols on hydrogenation. The enantiomeric excess of the optically active alcohols produced via hydrogenation catalysed by 6 ranges from about 50 to about 85%.

Comparison of 6 and Comparative Complex 7 in Ketone Hydrogenation

The activities of 6 and comparative complex 7 as catalysts in the hydrogenation of acetophenone are compared in Table 2. Surprisingly, the turnover frequencies (TOF) calculated when using 6 are consistently higher (at least 3.5 times higher) than when 7 is used. This is true even when lower catalyst loadings of 6 are used (see entries 1 and 4). The higher TOF when using 6 leads to a higher conversion of ketone to alcohol after 2 hours (56.5% conversion when using 6 compared with 9.4% when using 7).

Comparative Complex 7:

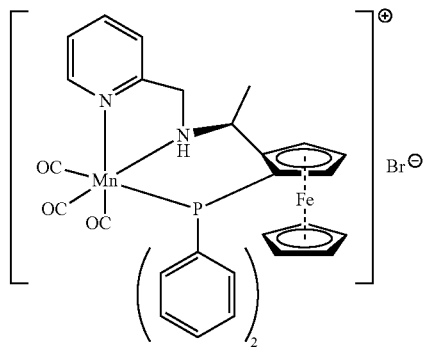

$(S_c,R_p)$-7

TABLE 2

Catalytic activity of 6 and comparative complex 7 in the hydrogenation of acetophenone.

50 bar $H_2$
5 mol % $K_2CO_3$
EtOH, 50° C.

Ph—C(=O)—CH$_3$ → Ph—CH(OH)—CH$_3$

| Catalyst | Method[a] | Catalyst Loading (mol %) | Reaction time (h) | Conversion (%) | TOF[b] ($h^{-1}$) |
|---|---|---|---|---|---|
| 7 | Gas uptake | 0.1 | 11.5 | 100 | 65 |
| 7 | Vial | 0.1 | 2 | 9.4 | 47 |
| 6 | Gas uptake | 0.1 | 6 | 100 | 230 |
| 6 | Gas uptake | 0.05 | 12 | 100 | 237 |
| 6 | Vial | 0.1 | 2 | 56.5 | 283 |

[a]gas uptake mean the use of an autoclave with a gas burette attached for measuring gas uptake, vial corresponds to microwave vials in a stainless-steel autoclave at 50 bar $H_2$ pressure for a set period of time;
[b]the turnover frequency (TOF) is equal to the number of molecules reacting per active site per hour, for vial data it was calculated after 2 h, for gas uptake it corresponds to 20% conversion.

Comparison of the Solubility of 6 and Comparative Complex 7

In the above experiments, catalyst 6 was found to dissolve far more readily for analysis, or for preparing catalysis solutions. The latter point makes experimental set up more convenient, and also increases the possible range of conditions that can be employed. The solubility (measured at 18° C.) of 6 and comparative complex 7 in solvents of varying polarities are compared in Table 3. Unexpectedly, the solubility of 6 is greater than that of 7 in all of the solvents tested. 6 is more soluble than 7 in both polar and non-polar solvents.

TABLE 3

Comparison in solubility between 6 and 7

| Catalyst | Solvent | Solubility (g/L) |
|---|---|---|
| 7 | Ethanol | 0.6 |
| 7 | Toluene | <0.4 |
| 7 | MeTHF | 2.7 |
| 6 | Ethanol | 32 |
| 6 | Toluene | 17 |
| 6 | MeTHF | 25 |

Method: To a known amount of pre-catalyst was added solvent in 0.1 mL aliquots until full dissolution was seen assessed via visual confirmation at room temperature.

The invention claimed is:
1. A method comprising hydrogenating a ketone in the presence of (i) a base, (ii) hydrogen gas and (iii) a catalyst comprising a charged or neutral complex of formula (I):

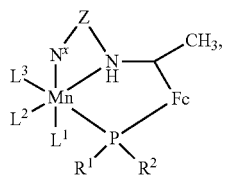

wherein:

Mn is a manganese atom or a manganese ion in oxidation state (I) to (VII);

$R^1$ and $R^2$ are each independently $C_{4-8}$monocyclic aryl or $C_{3-7}$monocyclic heteroaryl moieties, optionally substituted one or more times with a first electron donating group;

-Fc- denotes a ferrocene (bis($\eta^5$-cyclopentadienyl)iron) moiety covalently bonded via adjacent carbon atoms of one of the two cyclopentadienyl moieties, and which may be optionally further substituted, in either cyclopentadienyl ring, one or more times with a substituent selected from the group consisting of halo, aliphatic $C_{1-6}$hydrocarbyl, trihalomethyl, aryl, heteroaryl, hydroxy, nitro, amino, alkoxy, alkylthio, carboxylate, sulfonate, phosphate, cyano, thio, formyl, ester, acyl, thioacyl, carbamido and sulfonamido;

—Z— is an alkylene linker of the formula —$(CH_2)_{1-6}$— in which one or more of the hydrogen atoms of the alkylene may be independently substituted with an alkyl, aryl, heteroaryl, hydroxy, nitro, amino, alkoxy, alkylthio or thiol substituent;

—$N^x$ is a nitrogen-containing heteroaryl moiety, optionally substituted one or more times with a second electron donating group, with the proviso that at least one of $R^1$, $R^2$ and —$N^x$ is substituted one or more times with the first and/or second electron donating group respectively; and $L^1$-$L^3$ constitute one, two or three ligands in which each of $L^1$-$L^3$ independently represents a monodentate neutral or anionic ligand; or one of $L^1$-$L^3$ represents a monodentate neutral or anionic ligand and the other two of $L^1$-$L^3$ together represent a bidentate neutral or anionic ligand; or $L^1$-$L^3$ together represent a tridentate neutral or anionic ligand, wherein, when the complex of formula (I) is charged, the catalyst comprises one or more additional counterions to balance the charge of the complex.

2. The method of claim 1 wherein the base is selected from the group consisting of potassium carbonate, potassium phosphate, potassium hydroxide, potassium tert-butoxide, sodium tert-butoxide, sodium carbonate, cesium carbonate, sodium hydroxide, lithium carbonate, lithium hydroxide, calcium hydroxide, potassium bicarbonate, sodium bicarbonate, lithium bicarbonate, sodium methoxide and tertiary amines.

3. The method of claim 1 wherein the conjugate acid of the base has a pKa from 6.3 to 14.

4. The method of claim 1 wherein $R^1$ and $R^2$ are each optionally substituted phenyl moieties.

5. The method of claim 1 wherein the first electron donating group is any one or a combination selected from the group consisting of $C_{1-6}$alkyl and $C_{1-6}$alkoxy.

6. The method of claim 1 wherein $R^1$ and $R^2$ are the same.

7. The method of claim 1 wherein $R^1$ and $R^2$ are both 4-methoxy-3,5-dimethylphenyl or 4-methoxy-3,5-di-tert-butylphenyl.

8. The method of claim 1 wherein the $R^1R^2$P-Fc-CH(Me)-NH— component of the complex is 1-[bis(4-methoxy-3,5-dimethylphenyl)phosphino]-2-[1-(HN)ethyl]ferrocene, 1-[bis(4-methoxy-3,5-di-tert-butylphenyl)phosphino]-2-[1-(HN)ethyl]ferrocene or 1-[1-(HN)ethyl]-2-(diphenylphosphino)ferrocene.

9. The method of claim 1, wherein the second electron donating group is any one or a combination selected from the group consisting of amino and $C_{1-6}$alkyl.

10. The method of claim 1, wherein —$N^x$ is an optionally substituted pyridyl ring.

11. The method of claim 1 wherein —$N^x$ is 4-dimethylaminopyridin-2-yl or 2-pyridyl.

12. The method of claim 1 wherein $L^1$-$L^3$ constitute three ligands selected from neutral monodentate ligands and/or each of $L^1$-$L^3$ is the same.

13. The method of claim 12 wherein each of $L^1$-$L^3$ is carbon monoxide.

14. The method of claim 1, wherein the catalyst has any one of the formulae:

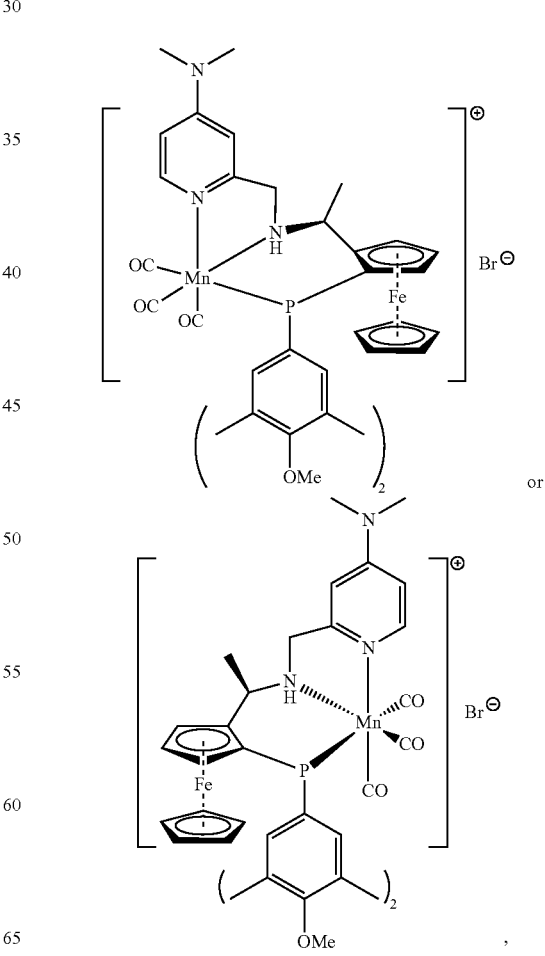

or is a mixture thereof;

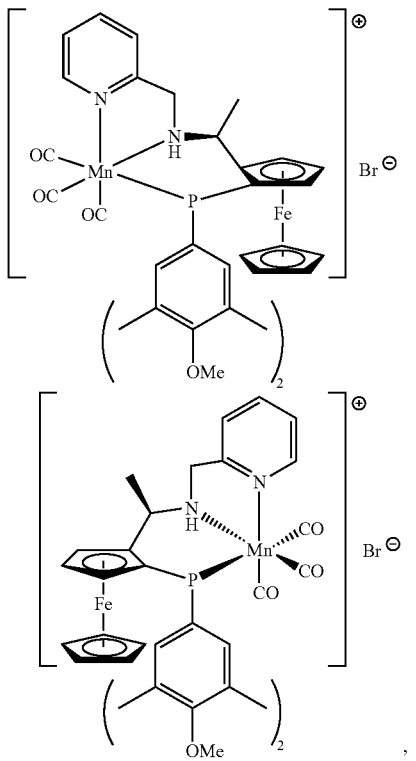

or is a mixture thereof;

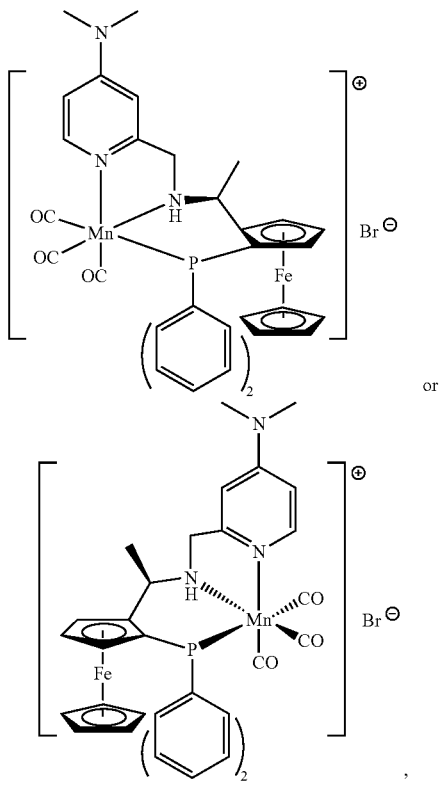

or is a mixture thereof;

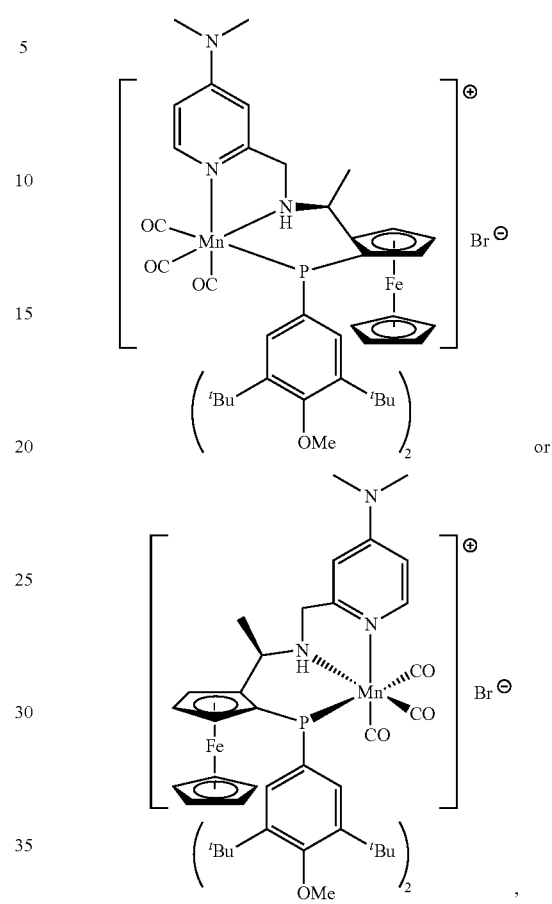

or is a mixture thereof.

15. The method of claim 1 wherein —$N^x$ is substituted one or more times with the second electron donating group and at least one of $R^1$ and $R^2$ are substituted one or more times with the first electron donating group.

16. The method of claim 1, wherein the catalyst has any one of the formulae:

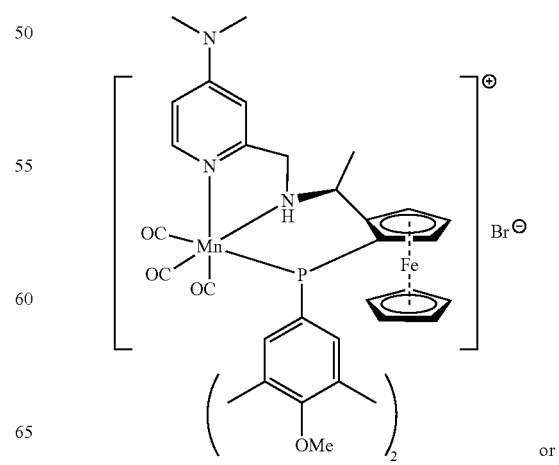

or

-continued

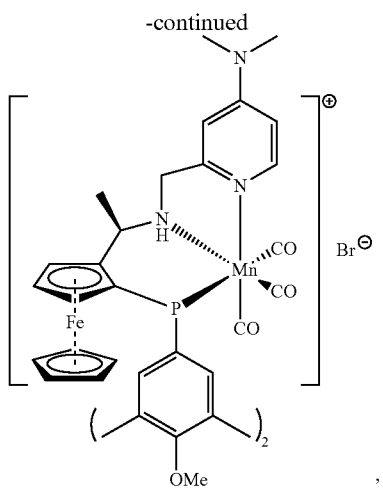

or is a mixture thereof.

17. The method of claim 1 wherein the ketone is prochiral.

18. The method of claim 17, wherein an optically active alcohol is provided by the hydrogenation with an enantiomeric excess of about 50 to about 90%.

19. A catalyst comprising a charged or neutral complex of formula (I):

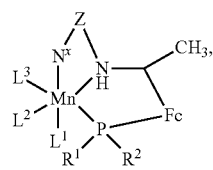
(I)

wherein:
Mn is a manganese atom or a manganese ion in oxidation state (I) to (VII);
$R^1$ and $R^2$ are each independently $C_{4-8}$monocyclic aryl or $C_{3-7}$monocyclic heteroaryl moieties, optionally substituted one or more times with a first electron donating group;
-Fc- denotes a ferrocene (bis($\eta^5$-cyclopentadienyl)iron) moiety covalently bonded via adjacent carbon atoms of one of the two cyclopentadienyl moieties, and which may be optionally further substituted, in either cyclopentadienyl ring, one or more times with a substituent selected from the group consisting of halo, aliphatic $C_{1-6}$ hydrocarbyl, trihalomethyl, aryl, heteroaryl, hydroxy, nitro, amino, alkoxy, alkylthio, carboxylate, sulfonate, phosphate, cyano, thio, formyl, ester, acyl, thioacyl, carbamido and sulfonamido;
—Z— is an alkylene linker of the formula —$(CH_2)_{1-6}$— in which one or more of the hydrogen atoms of the alkylene may be independently substituted with an alkyl, aryl, heteroaryl, hydroxy, nitro, amino, alkoxy, alkylthio or thiol substituent;
—$N^x$ is a nitrogen-containing heteroaryl moiety, wherein —$N^x$ is substituted one or more times with a second electron donating group and at least one of $R^1$ and $R^2$ are substituted one or more times with the first electron donating group; and
$L^1$-$L^3$ constitute one, two or three ligands in which each of $L^1$-$L^3$ independently represents a monodentate neutral or anionic ligand: or one of $L^1$-$L^3$ represents a monodentate neutral or anionic ligand and the other two of $L^1$-$L^3$ together represent a bidentate neutral or anionic ligand; or $L^1$-$L^3$ together represent a tridentate neutral or anionic ligand,
wherein, when the complex of formula (I) is charged, the catalyst comprises one or more additional counterions to balance the charge of the complex.

20. A compound comprising a charged or neutral complex of formula (I):

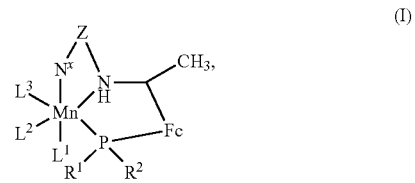
(I)

wherein:
Mn is a manganese atom or a manganese ion in oxidation state (I) to (VII);
$R^1$ and $R^2$ are each independently $C_{4-8}$monocyclic aryl or $C_{3-7}$monocyclic heteroaryl moieties, optionally substituted one or more times with a first electron donating group;
-Fc- denotes a ferrocene (bis($\eta^5$-cyclopentadienyl)iron) moiety covalently bonded via adjacent carbon atoms of one of the two cyclopentadienyl moieties, and which may be optionally further substituted, in either cyclopentadienyl ring, one or more times with a substituent selected from the group consisting of halo, aliphatic $C_{1-6}$ hydrocarbyl, trihalomethyl, aryl, heteroaryl, hydroxy, nitro, amino, alkoxy, alkylthio, carboxylate, sulfonate, phosphate, cyano, thio, formyl, ester, acyl, thioacyl, carbamido and sulfonamido;
—Z— is an alkylene linker of the formula —$(CH_2)_{1-6}$— in which one or more of the hydrogen atoms of the alkylene may be independently substituted with an alkyl, aryl, heteroaryl, hydroxy, nitro, amino, alkoxy, alkylthio or thiol substituent;
—$N^x$ is a nitrogen-containing heteroaryl moiety, wherein —$N^x$ is substituted one or more times with a second electron donating group and at least one of $R^1$ and $R^2$ are substituted one or more times with the first electron donating group; and
$L^1$-$L^3$ constitute one, two or three ligands in which each of $L^1$-$L^3$ independently represents a monodentate neutral or anionic ligand; or one of $L^1$-$L^3$ represents a monodentate neutral or anionic ligand and the other two of $L^1$-$L^3$ together represent a bidentate neutral or anionic ligand; or $L^1$-$L^3$ together represent a tridentate neutral or anionic ligand,
wherein, when the complex of formula (I) is charged, the catalyst comprises one or more additional counterions to balance the charge of the complex.

* * * * *